(12) United States Patent
Lee et al.

(10) Patent No.: US 9,493,745 B2
(45) Date of Patent: Nov. 15, 2016

(54) HEXON ISOLATED FROM SIMIAN ADENOVIRUS SEROTYPE 19, HYPERVARIABLE REGION THEREOF AND CHIMERIC ADENOVIRUS USING THE SAME

(71) Applicant: MOGAM BIOTECHNOLOGY RESEARCH INSTITUTE, Yongin-Si (KR)

(72) Inventors: Kyuhyun Lee, Yongin-si (KR); Seongtae Yun, Yongin-si (KR); Daekyung Koh, Yongin-si (KR); Hong-Kyu Lee, Yongin-si (KR); Eui-Cheol Jo, Yongin-si (KR)

(73) Assignee: MOGAM BIOTECHNOLOGY RESEARCH INSTITUTE, Yongin-Si (KR)

( * ) Notice: Subject to any disclaimer, the term of this patent is extended or adjusted under 35 U.S.C. 154(b) by 0 days.

(21) Appl. No.: 14/521,864

(22) Filed: Oct. 23, 2014

(65) Prior Publication Data

US 2015/0111282 A1    Apr. 23, 2015

Related U.S. Application Data

(62) Division of application No. 13/641,027, filed as application No. PCT/KR2010/002298 on Apr. 14, 2010, now abandoned.

(51) Int. Cl.

| | |
|---|---|
| *A61K 35/76* | (2015.01) |
| *C12N 15/861* | (2006.01) |
| *A61P 35/00* | (2006.01) |
| *C12N 15/34* | (2006.01) |
| *C12N 5/10* | (2006.01) |
| *C12N 7/00* | (2006.01) |
| *C07K 14/005* | (2006.01) |
| *C12N 15/86* | (2006.01) |

(52) U.S. Cl.
CPC ............... *C12N 7/00* (2013.01); *C07K 14/005* (2013.01); *C12N 15/86* (2013.01); *C12N 2710/10322* (2013.01); *C12N 2710/10332* (2013.01); *C12N 2710/10343* (2013.01); *C12N 2710/10345* (2013.01); *C12N 2810/6018* (2013.01)

(58) Field of Classification Search
None
See application file for complete search history.

(56) References Cited

U.S. PATENT DOCUMENTS

| | | | |
|---|---|---|---|
| 2005/0069866 A1 * | 3/2005 | Wilson | C07K 14/005 435/5 |
| 2009/0074810 A1 | 3/2009 | Roy et al. | |
| 2009/0098126 A1 | 4/2009 | Ebner | |
| 2011/0123522 A1 | 5/2011 | Arber | |

FOREIGN PATENT DOCUMENTS

| | | |
|---|---|---|
| WO | 98/40509 A1 | 9/1998 |
| WO | 2005/001103 A2 | 1/2005 |
| WO | 2006/040330 A2 | 4/2006 |
| WO | 2009/098492 A2 | 8/2009 |

OTHER PUBLICATIONS

Bradley et al, Adenovirus Serotype 5-Specific Neutralizing Antibodies Target Multiple Hexon Hypervariable Regions, Journal of Virology p. 1267-1272.*
Youil et al., "Hexon Gene Switch Strategy for the Generation of Chimeric Recombinant Adenovirus," Human Gene Therapy, 2002, vol. 13, No. 2, pp. 311-320.
European Patent Office, European Search Report issued in corresponding EP Application No. 10849873.4, dated Sep. 4, 2013.

* cited by examiner

*Primary Examiner* — Maria Marvich
(74) *Attorney, Agent, or Firm* — Sughrue Mion, PLLC

(57) ABSTRACT

Novel hexon isolated from simian adenovirus serotype 19 encoded in the polynucleotide defined as SEQ ID NO: 3, hepervariable region thereof, chimeric adenovirus comprising the same, and therapeutic use thereof provides a solution to the problem of safety and effective systemic treatment for developing gene therapeutic agents using adenovirus.

11 Claims, 33 Drawing Sheets

FIG. 1A

```
                    1                                                  50
Ad5 Hexon      (1)  MATPSMMPQWSYMHISGQDASEYLSPGLVQFARATETYFSLNNKFRNPTV
SAd19 Hexon    (1)  MATPSMMPQWSYMHIAGQDASEYLSPGLVQFARATDTYFSLGNKFRNPTV
Consensus      (1)  MATPSMMPQWSYMHI GQDASEYLSPGLVQFARATDTYFSL NKFRNPTV
                    51                                                100
Ad5 Hexon     (51)  APTHDVTTDRSQRLTLRFIPVDREDTAYSYKARFTLAVGDNRVLDMASTY
SAd19 Hexon   (51)  APTHDVTTDRSQRLTLRFVPVDREDTAYSYKVRFTLAVGDNRVLDMASTY
Consensus     (51)  APTHDVTTDRSQRLTLRF PVDREDTAYSYK RFTLAVGDNRVLDMASTY
                    101                                               150
Ad5 Hexon    (101)  FDIRGVLDRGPTFKPYSGTAYNALAPKGAPNPCEWDEAATALEINLEEED
SAd19 Hexon  (101)  FDIRGTLDRGPSFKPYSGTAYNALAPKGAPNACQWTTTN---------G
Consensus    (101)  FDIRG LDRGPSFKPYSGTAYNALAPKGAPN C W
                    151                                               200
Ad5 Hexon    (151)  DDNEDEVDEQAEQQKTHVFGQAPYSGINITKEG-------IQIGVEGQTP
SAd19 Hexon  (141)  ----G--------NKTNSFAQAPVIGLSIDATNGLKVGEEIPATGGANTP
Consensus    (151)              NKT FAQAP GI I         I    ANTP
                    201                                               250
Ad5 Hexon    (194)  KYADKTFQPEPQIGESQWYETEINHAAGRVLKKTTPMKPCYGSYAKPTNE
SAd19 Hexon  (179)  VYADKTFQPEPQVGETKWNSNPTENAAGRILKPNTPMQPCYGSYARPTNE
Consensus    (201)   YADKTFQPEPQIGES W       AAGRILK TPM PCYGSYAKPTNE
                    251                                               300
Ad5 Hexon    (244)  NGGQGILVKQ-QNGKLESQVEMQFFSTTEATAGNGDNLTPKVVLYSEDVD
SAd19 Hexon  (229)  KGGQAKLVTNGQDNQTTPDVSLNFFTTASETT----TFTPKVVLYSENVN
Consensus    (251)   GGQA LV N Q       V LNFFST T     TPKVVLYSE V
                    301                                               350
Ad5 Hexon    (293)  IETPDTHISYMPTIKE--GNSRELMGQQSMPNRPNYIAFRDNFIGLMYYN
SAd19 Hexon  (275)  LEAPDTHLVYKPDGTDGITNAETLLGLQSAPNRPNYIGFRDNFIGLMYYN
Consensus    (301)  IE PDTHI Y P  D   NA  LLG QS PNRPNYI FRDNFIGLMYYN
                    351                                               400
Ad5 Hexon    (341)  STGNMGVLAGQASQLNAVVDLQDRNTELSYQLLLDSIGDRTRYFSMWNQA
SAd19 Hexon  (325)  STGNMGVLAGQASQLNAVVDLQDRNTELSYQLMLDALGDRSRYFSMWNQA
Consensus    (351)  STGNMGVLAGQASQLNAVVDLQDRNTELSYQLLLDA IGDRSRYFSMWNQA
                    401                                               450
Ad5 Hexon    (391)  VDSYDPDVRIIENHGTEDELPNYCFPLGGVINTETLTKVKPKTGQENGWE
SAd19 Hexon  (375)  VDSYDPDVRIIENHGVEDELPNYCFPLNAQGVANTYQGVKNGSGN---WS
Consensus    (401)  VDSYDPDVRIIENHG EDELPNYCFPL  A   T  VK SGN    W
                    451                                               500
Ad5 Hexon    (441)  KDATEFSDKNEIRVGNNFAMEINLNANLWRNFLYSNIALYLPDKLKYSPS
SAd19 Hexon  (422)  KDTNVG-TANEIGIGNIFAFEINLAANLWRSFLYSNVALYLPDAYKLTPD
Consensus    (451)  KD     NEI  IGN FA EINL ANLWR FLYSNIALYLPD K SP
```

FIG. 1A (continued)

```
                  501                                                550
Ad5 Hexon    (491) NVKISDNPNTYDYMNKRVVAPGLVDCYINLGARWSLDYMDNVNPFNHHRN
SAd19 Hexon  (471) NITLPDNKNTYEYINGRVAAPASLDTYVNIGARWSPDPMDNVNPFNHHRN
Consensus    (501) NI I DN NTYDYIN RV APA LD YINI GARWS D MDNVNPFNHHRN
                  551                                                600
Ad5 Hexon    (541) AGLRYRSMLLGNGRYVPFHIQVPQKFFAIKNLLLLPGSYTYEWNFRKDVN
SAd19 Hexon  (521) AGLRYRSMLLGNGRYVPFHIQVPQKFFAIKNLLLLPGSYTYEWNFRKDVN
Consensus    (551) AGLRYRSMLLGNGRYVPFHIQVPQKFFAIKNLLLLPGSYTYEWNFRKDVN
                  601                                                650
Ad5 Hexon    (591) MVLQSSLGNDLRVDGASIKFDSICLYATFFPMAHNTASTLEAMLRNDTND
SAd19 Hexon  (571) MILQSTLGNDLRVDGASVRFDSINLYANFFPMAHNTASTLEAMLRNDTND
Consensus    (601) MI LQSSLGNDLRVDGASI KFDSI LYA FFPMAHNTASTLEAMLRNDTND
                  651                                                700
Ad5 Hexon    (641) QSFNDYLSAANMLYPIPANATNVPISIPSRNWAAFRGWAFTRLKTKETPS
SAd19 Hexon  (621) QSFNDYLCAANMLYPIPANATSVPISIPSRNWAAFRGWSFTRLKTRETPS
Consensus    (651) QSFNDYL AANMLYPIPANAT VPISIPSRNWAAFRGWAFTRLKTKETPS
                  701                                                750
Ad5 Hexon    (691) LGSGYDPYYTYSGSIPYLDGTFYLNHTFKKVAITFDSSVSWPGNDRLLTP
SAd19 Hexon  (671) LGSGFDPYFVYSGSIPYLDGTFYLNHTFKKVSIMFDSSVSWPGNDRLLTP
Consensus    (701) LGSGFDPYF YSGSIPYLDGTFYLNHTFKKVAI FDSSVSWPGNDRLLTP
                  751                                                800
Ad5 Hexon    (741) NEFEIKRSVDGEGYNVAQCNMTKDWFLVQMLANYNIGYQGFYIPESYKDR
SAd19 Hexon  (721) NEFEIKRSVDGEGYNVAQSNMTKDWFLIQMLSHYNIGYQGFYVPESYKDR
Consensus    (751) NEFEIKRSVDGEGYNVAQ NMTKDWFLIQMLA YNIGYQGFYIPESYKDR
                  801                                                850
Ad5 Hexon    (791) MYSFFRNFQPMSRQVVDDTKYKDYQQVGILHQHNNSGFVGYLAPTMREGQ
SAd19 Hexon  (771) MYSFFRNFQPMSRQVVDPVNYTNYKEVTLPYQHNNSGFVGYMGPTMREGQ
Consensus    (801) MYSFFRNFQPMSRQVVD   Y Y V I HQHNNSGFVGYLAPTMREGQ
                  851                                                900
Ad5 Hexon    (841) AYPANFPYPLIGKTAVDSITQKKFLCDRTLWRIPFSSNFMSMGALTDLGQ
SAd19 Hexon  (821) AYPANYPYPLIGKTAVPSLTQKKFLCDRVMWRIPFSSNFMSMGALTDLGQ
Consensus    (851) AYPANFPYPLIGKTAV SITQKKFLCDR LWRIPFSSNFMSMGALTDLGQ
                  901                                                950
Ad5 Hexon    (891) NLLYANSAHALDMTFEVDPMDEPTLLYVLFEVFDVVRVHRPHRGVIETVY
SAd19 Hexon  (871) NMLYANSAHALDMTFEVDPMDEPTLLYVLFEVFDVVRIHQPHRGVIEAVY
Consensus    (901) NLLYANSAHALDMTFEVDPMDEPTLLYVLFEVFDVVRIH PHRGVIE VY
                  951    963
Ad5 Hexon    (941) LRTPFSAGNATT-
SAd19 Hexon  (921) LRTPFSAGNATT-
Consensus    (951) LRTPFSAGNATT
```

FIG. 1B

```
                          1                                                50
Ad41 Hexon      (1)   MATPSMMPQWSYMHI AGQDASEYLSPGLVQFARATDTYFSLGNKFRNPTV
SAd19 Hexon     (1)   MATPSMMPQWSYMHI AGQDASEYLSPGLVQFARATDTYFSLGNKFRNPTV
Consensus       (1)   MATPSMMPQWSYMHI AGQDASEYLSPGLVQFARATDTYFSLGNKFRNPTV
                         51                                               100
Ad41 Hexon     (51)   APTHDVTTDRSQRLTLRFVPVDREDTAYSYKVRFTLAVGDNRVLDMASTY
SAd19 Hexon    (51)   APTHDVTTDRSQRLTLRFVPVDREDTAYSYKVRFTLAVGDNRVLDMASTY
Consensus      (51)   APTHDVTTDRSQRLTLRFVPVDREDTAYSYKVRFTLAVGDNRVLDMASTY
                        101                                               150
Ad41 Hexon    (101)   FDIRGVLDRGPSFKPYSGTAYNSLAPKTAPNPCEWKDNN---KIKVRGQA
SAd19 Hexon   (101)   FDIRGTLDRGPSFKPYSGTAYNALAPKGAPNACQWTTTNGGNKTNSFAQA
Consensus     (101)   FDIRG LDRGPSFKPYSGTAYN LAPK APN C W   N    K   AQA
                        151                                               200
Ad41 Hexon    (148)   PFIGTNINKDNGIQIGTDT-----TNQPIYADKTYQPEPQVGQTQWNSEV
SAd19 Hexon   (151)   PVIGLSIDATNGLKVGEEIPATGGANTPVYADKTFQPEPQVGETKWNSNP
Consensus     (151)   P IG   I   NGI IG D       N P YADKTFQPEPQVG T WNS
                        201                                               250
Ad41 Hexon    (193)   GAAQKVAGRVLKDTTPMLPCYGSYAKPTNEKGGQASLITNGTDQTLTSDV
SAd19 Hexon   (201)   --TENAAGRILKPNTPMQPCYGSYARPTNEKGGDAKLVTNGQDNQTTPDV
Consensus     (201)          AGRILK TPM PCYGSYAKPTNEKGGQ A LITNG DN  T D
                        251                                               300
Ad41 Hexon    (243)   NLQFFALPSTPN--EPKAVLYAENVSIEAPDTHLVYKPDVAQGTISSADL
SAd19 Hexon   (249)   SLNFFTTASETTTFTPKVVLYSENVNLEAPDTHLVYKPDGTDGITNAETL
Consensus     (251)    LNFF  S    PK VLYAENV IEAPDTHLVYKPD   G  A  L
                        301                                               350
Ad41 Hexon    (291)   LTQQAAPNRPNYIGFRDNFIGLMYYNSTGNMGVLAGQASQLNAWDLQDR
SAd19 Hexon   (299)   LGLQSAPNRPNYIGFRDNFIGLMYYNSTGNMGVLAGQASQLNAWDLQDR
Consensus     (301)   L  QAAPNRPNYIGFRDNFIGLMYYNSTGNMGVLAGQASQLNAWDLQDR
                        351                                               400
Ad41 Hexon    (341)   NTELSYQLMLDALGDRSRYFSMWNQAVDSYDPDVRIIENHGVEDELPNYC
SAd19 Hexon   (349)   NTELSYQLMLDALGDRSRYFSMWNQAVDSYDPDVRIIENHGVEDELPNYC
Consensus     (351)   NTELSYQLMLDALGDRSRYFSMWNQAVDSYDPDVRIIENHGVEDELPNYC
                        401                                               450
Ad41 Hexon    (391)   FPLGGSAATDTYSGIKANGQTWTAQDNYADRGAEIESGNIFAMEINLAAN
SAd19 Hexon   (399)   FPLNAQGVANTYQGVKNGSGNWSKDTNVG-TANEIGIGNIFAFEINLAAN
Consensus     (401)   FPL A A  TY GIK    WS D N  A   EI  GNIFA EINLAAN
```

FIG. 1B (continued)

```
                      451                                                500
Ad41 Hexon     (441) LWRSFLYSNVALYLPDSYKITPDNITLPENKNTYAYMNGRVAVPSALDTY
SAd19 Hexon    (448) LWRSFLYSNVALYLPDAYKLTPDNITLPDNKNTYEYINGRVAAPASLDTY
Consensus      (451) LWRSFLYSNVALYLPDAYKITPDNITLPDNKNTY YINGRVA PAALDTY
                      501                                                550
Ad41 Hexon     (491) VNIGARWSPDPMDNVNPFNHHRNAGLRYRSMLLGNGRYVPFHIQVPQKFF
SAd19 Hexon    (498) VNIGARWSPDPMDNVNPFNHHRNAGLRYRSMLLGNGRYVPFHIQVPQKFF
Consensus      (501) VNIGARWSPDPMDNVNPFNHHRNAGLRYRSMLLGNGRYVPFHIQVPQKFF
                      551                                                600
Ad41 Hexon     (541) AIKNLLLLPGSYTYEWNFRKDVNMILQSSLGNDLRVDGASVRFDSINLYA
SAd19 Hexon    (548) AIKNLLLLPGSYTYEWNFRKDVNMILQSTLGNDLRVDGASVRFDSINLYA
Consensus      (551) AIKNLLLLPGSYTYEWNFRKDVNMILQSSLGNDLRVDGASVRFDSINLYA
                      601                                                650
Ad41 Hexon     (591) NFFPMWHNTASTLEAMLRNDTNDQSFNDYLCAANMLYPIPSNATSVPISI
SAd19 Hexon    (598) NFFPMWHNTASTLEAMLRNDTNDQSFNDYLCAANMLYPIPANATSVPISI
Consensus      (601) NFFPMWHNTASTLEAMLRNDTNDQSFNDYLCAANMLYPIPANATSVPISI
                      651                                                700
Ad41 Hexon     (641) PSRNWAAFRGWSFTRLKTKETPSLGSGFDPYFTYSGSVPYLDGTFYLNHT
SAd19 Hexon    (648) PSRNWAAFRGWSFTRLKTRETPSLGSGFDPYFVYSGSIPYLDGTFYLNHT
Consensus      (651) PSRNWAAFRGWSFTRLKTKETPSLGSGFDPYF YSGSIPYLDGTFYLNHT
                      701                                                750
Ad41 Hexon     (691) FKKVSIMFDSSVSWPGNDRLLTPNEFEIKRTVDGEGYNVAQCNMTKDWFL
SAd19 Hexon    (698) FKKVSIMFDSSVSWPGNDRLLTPNEFEIKRSVDGEGYNVAQSNMTKDWFL
Consensus      (701) FKKVSIMFDSSVSWPGNDRLLTPNEFEIKRSVDGEGYNVAQ NMTKDWFL
                      751                                                800
Ad41 Hexon     (741) IQMLSHYNIGYQGFYVPESYKDRMYSFFRNFQPMSRQVVNTTTYKEYQNV
SAd19 Hexon    (748) IQMLSHYNIGYQGFYVPESYKDRMYSFFRNFQPMSRQVVDPVNYTNYKEV
Consensus      (751) IQMLSHYNIGYQGFYVPESYKDRMYSFFRNFQPMSRQVV   Y Y  V
                      801                                                850
Ad41 Hexon     (791) TLPFQHNNSGFVGYMGPTMREGQAYPANYPYPLIGQTAVPSLTQKKFLCD
SAd19 Hexon    (798) TLPYQHNNSGFVGYMGPTMREGQAYPANYPYPLIGKTAVPSLTQKKFLCD
Consensus      (801) TLPFQHNNSGFVGYMGPTMREGQAYPANYPYPLIG TAVPSLTQKKFLCD
                      851                                                900
Ad41 Hexon     (841) RTMWRIPFSSNFMSMGALTDLGQNMLYANSAHALDMTFEVDPMDEPTLLY
SAd19 Hexon    (848) RVMWRIPFSSNFMSMGALTDLGQNMLYANSAHALDMTFEVDPMDEPTLLY
Consensus      (851) R MWRIPFSSNFMSMGALTDLGQNMLYANSAHALDMTFEVDPMDEPTLLY
                      901                      936
Ad41 Hexon     (891) VLFEVFDVVRIHQPHRGVIEAVYLRTPFSAGNATT-
SAd19 Hexon    (898) VLFEVFDVVRIHQPHRGVIEAVYLRTPFSAGNATT-
Consensus      (901) VLFEVFDVVRIHQPHRGVIEAVYLRTPFSAGNATT
```

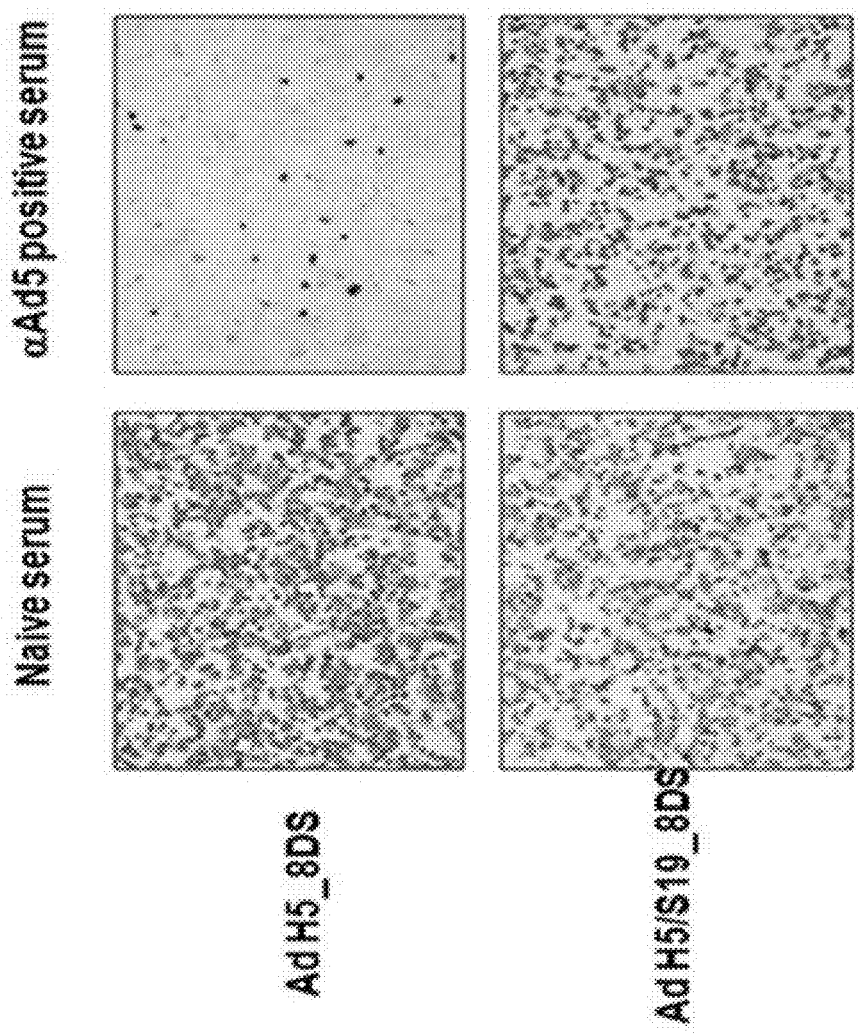

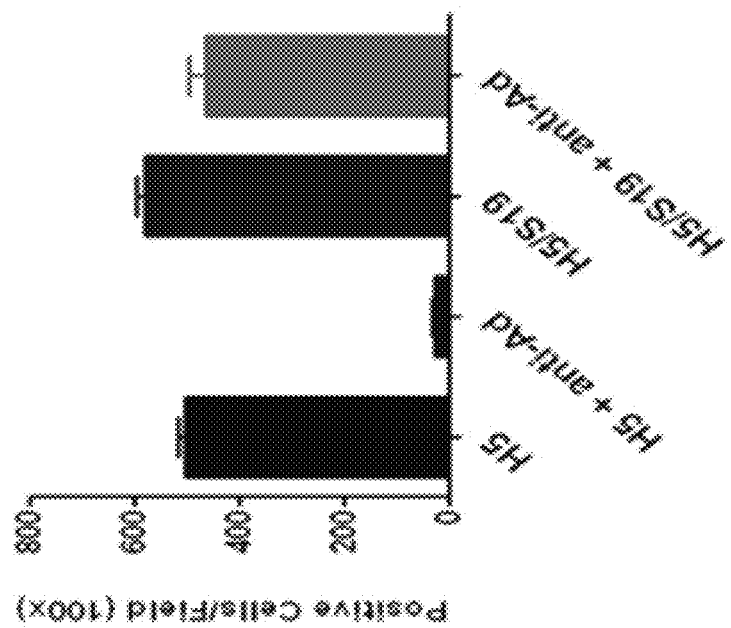

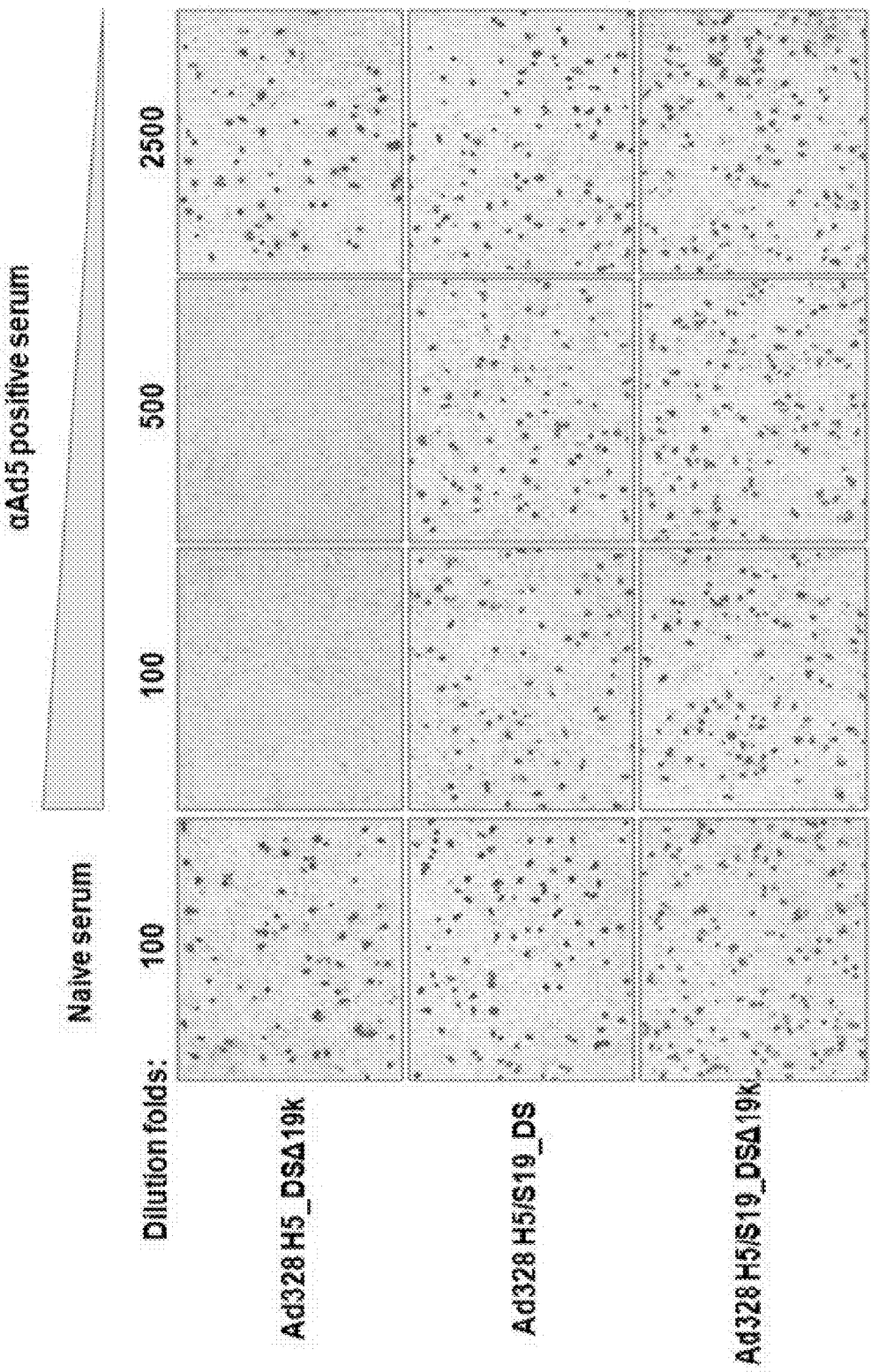

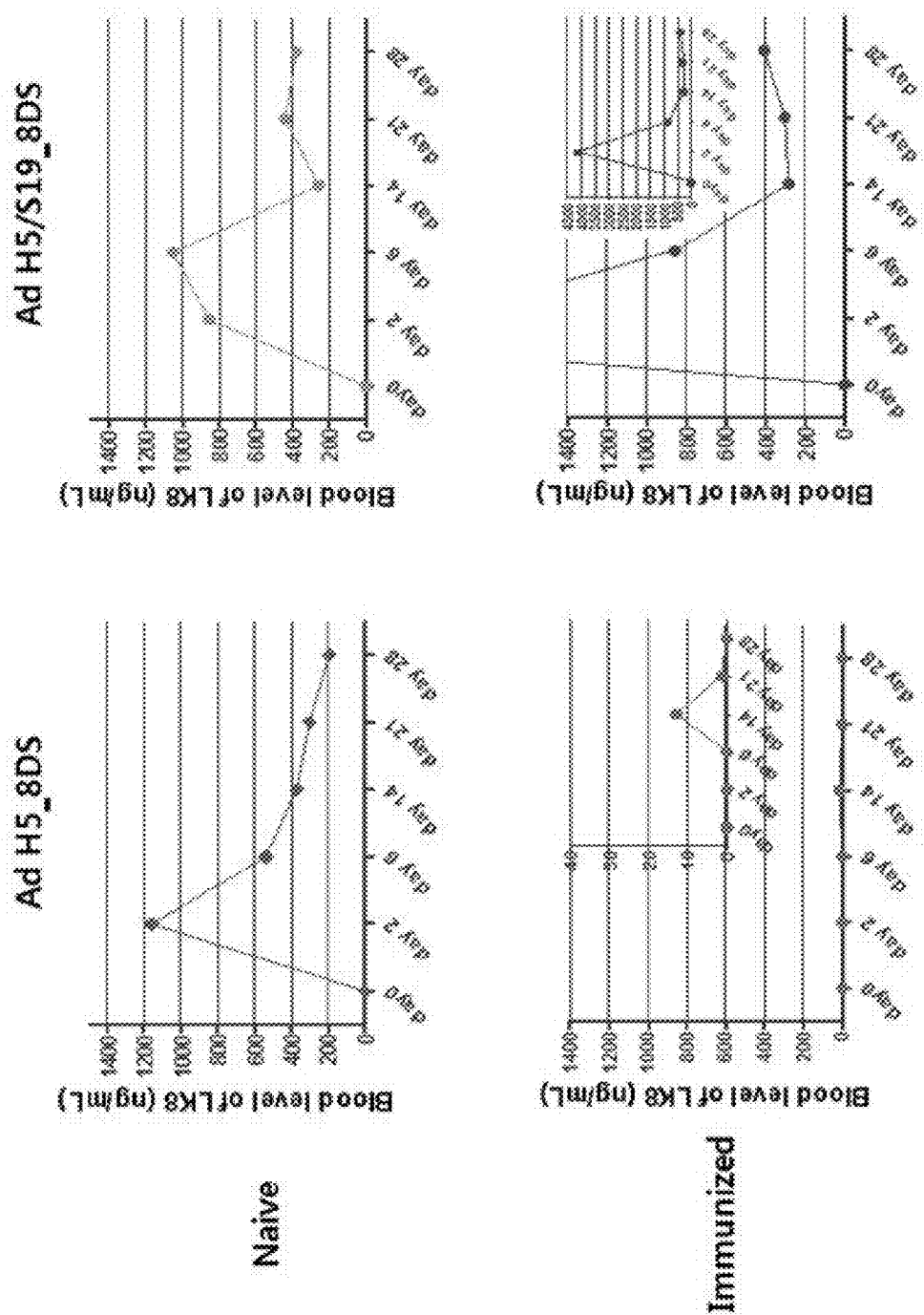

FIG. 10(A)

| | 5e+10 VP | 1e+10 VP | 5e+9 VP | 1e+9 VP | PBS |
|---|---|---|---|---|---|
| RBC(10^12/L) | 10.16 ± 0.45 | 9.50 ± 0.32 | 9.58 ± 0.46 | 9.50 ± 0.40 | 9.62 ± 0.58 |
| WBC(10^9/L) | 9.28 ± 0.20 | 8.52 ± 0.08 | 8.50 ± 1.30 | 8.18 ± 0.85 | 8.02 ± 0.72 |
| HCT (%) | 61.20 ± 2.10 | 58.80 ± 1.98 | 59.40 ± 2.20 | 59.40 ± 1.50 | 58.80 ± 2.50 |
| Hb (g/dL) | 17.80 ± 1.20 | 16.00 ± 0.84 | 15.40 ± 0.93 | 15.80 ± 0.58 | 14.80 ± 0.80 |
| Platelet (10^9/L) | 1292.00 ± 63.20 | 1314.00 ± 45.01 | 1448.00 ± 91.51 | 1400.00 ± 64.54 | 1390.00 ± 233.69 |
| MCV (fL) | 602.00 ± 5.50 | 619.00 ± 2.76 | 619.00 ± 8.16 | 620.00 ± 11.25 | 611.80 ± 12.85 |
| MCH (pg) | 174.00 ± 5.39 | 167.80 ± 2.88 | 163.00 ± 2.06 | 165.00 ± 2.35 | 154.40 ± 1.50 |
| MCHC (g/dL) | 286.80 ± 10.70 | 271.40 ± 4.53 | 264.00 ± 5.78 | 262.00 ± 4.82 | 252.80 ± 3.88 |
| B. Neutro (%) | 0.00 ± 0.00 | 0.00 ± 0.00 | 0.00 ± 0.00 | 0.00 ± 0.00 | 0.00 ± 0.00 |
| S. Neutro (%) | 12.74 ± 2.35 | 12.78 ± 3.03 | 12.00 ± 1.41 | 12.32 ± 1.72 | 10.42 ± 1.88 |
| Lymphocyte (%) | 81.78 ± 2.42 | 80.92 ± 3.53 | 81.46 ± 1.75 | 81.10 ± 2.11 | 83.74 ± 1.98 |
| Monocyte (%) | 1.24 ± 0.12 | 1.28 ± 0.24 | 1.00 ± 0.10 | 1.24 ± 0.25 | 1.52 ± 0.20 |
| Eosinophil (%) | 4.08 ± 0.35 | 4.98 ± 0.08 | 4.24 ± 0.98 | 5.32 ± 0.51 | 4.26 ± 0.38 |
| Basophil (%) | 0.16 ± 0.08 | 0.04 ± 0.04 | 0.04 ± 0.04 | 0.02 ± 0.02 | 0.06 ± 0.06 |

FIG. 11(A)

| | 1e+11 VP | 5e+10 VP | 1e+10 VP | 5e+9 VP | 1e+9 VP | PBS |
|---|---|---|---|---|---|---|
| RBC (10^6/μL) | 9.24 ± 0.29 | 9.86 ± 0.27 | 9.38 ± 0.33 | 9.52 ± 0.25 | 9.82 ± 0.43 | 9.02 ± 0.58 |
| WBC (10^3/μL) | 8.44 ± 0.52 | 9.16 ± 0.39 | 7.64 ± 0.46 | 8.40 ± 0.54 | 9.74 ± 1.18 | 8.02 ± 0.72 |
| HCT (%) | 57.20 ± 2.08 | 61.00 ± 1.58 | 59.40 ± 1.98 | 61.20 ± 1.38 | 62.00 ± 2.08 | 58.00 ± 2.58 |
| Hb (g/dL) | 14.00 ± 0.58 | 15.00 ± 0.48 | 15.40 ± 0.68 | 15.40 ± 0.51 | 16.20 ± 0.73 | 14.80 ± 0.68 |
| Platelet (10^3/μL) | 1204.00 ± 46.34 | 1426.00 ± 57.06 | 1444.00 ± 36.76 | 1466.00 ± 65.24 | 1544.00 ± 44.24 | 1388.00 ± 233.08 |
| MCV (fL) | 619.00 ± 5.70 | 617.40 ± 5.37 | 633.60 ± 4.48 | 648.20 ± 3.17 | 651.00 ± 3.36 | 611.00 ± 12.05 |
| MCH (pg) | 160.20 ± 2.98 | 162.00 ± 1.94 | 163.40 ± 2.23 | 162.00 ± 1.87 | 164.00 ± 2.36 | 154.40 ± 1.58 |
| MCHC (g/dL) | 258.00 ± 4.16 | 263.40 ± 3.14 | 258.20 ± 4.55 | 253.20 ± 2.65 | 260.00 ± 2.24 | 252.00 ± 3.88 |
| B. Neutro (%) | 0.00 ± 0.00 | 0.00 ± 0.00 | 0.00 ± 0.00 | 0.00 ± 0.00 | 0.00 ± 0.00 | 0.00 ± 0.00 |
| S. Neutro (%) | 9.48 ± 1.11 | 11.90 ± 0.52 | 10.64 ± 0.98 | 10.72 ± 0.55 | 11.04 ± 1.12 | 10.42 ± 1.08 |
| Lymphocyte (%) | 83.30 ± 1.64 | 82.16 ± 0.72 | 84.14 ± 1.29 | 84.96 ± 1.35 | 84.18 ± 0.78 | 83.74 ± 1.58 |
| Monocyte (%) | 1.44 ± 0.24 | 1.24 ± 0.22 | 1.12 ± 0.14 | 0.94 ± 0.12 | 1.46 ± 0.17 | 1.52 ± 0.28 |
| Eosinophil (%) | 5.78 ± 1.11 | 4.66 ± 0.68 | 4.10 ± 0.87 | 3.74 ± 0.40 | 3.32 ± 0.28 | 4.26 ± 0.38 |
| Basophil (%) | 0.00 ± 0.04 | 0.04 ± 0.02 | 0.00 ± 0.00 | 0.02 ± 0.02 | 0.00 ± 0.00 | 0.06 ± 0.06 |

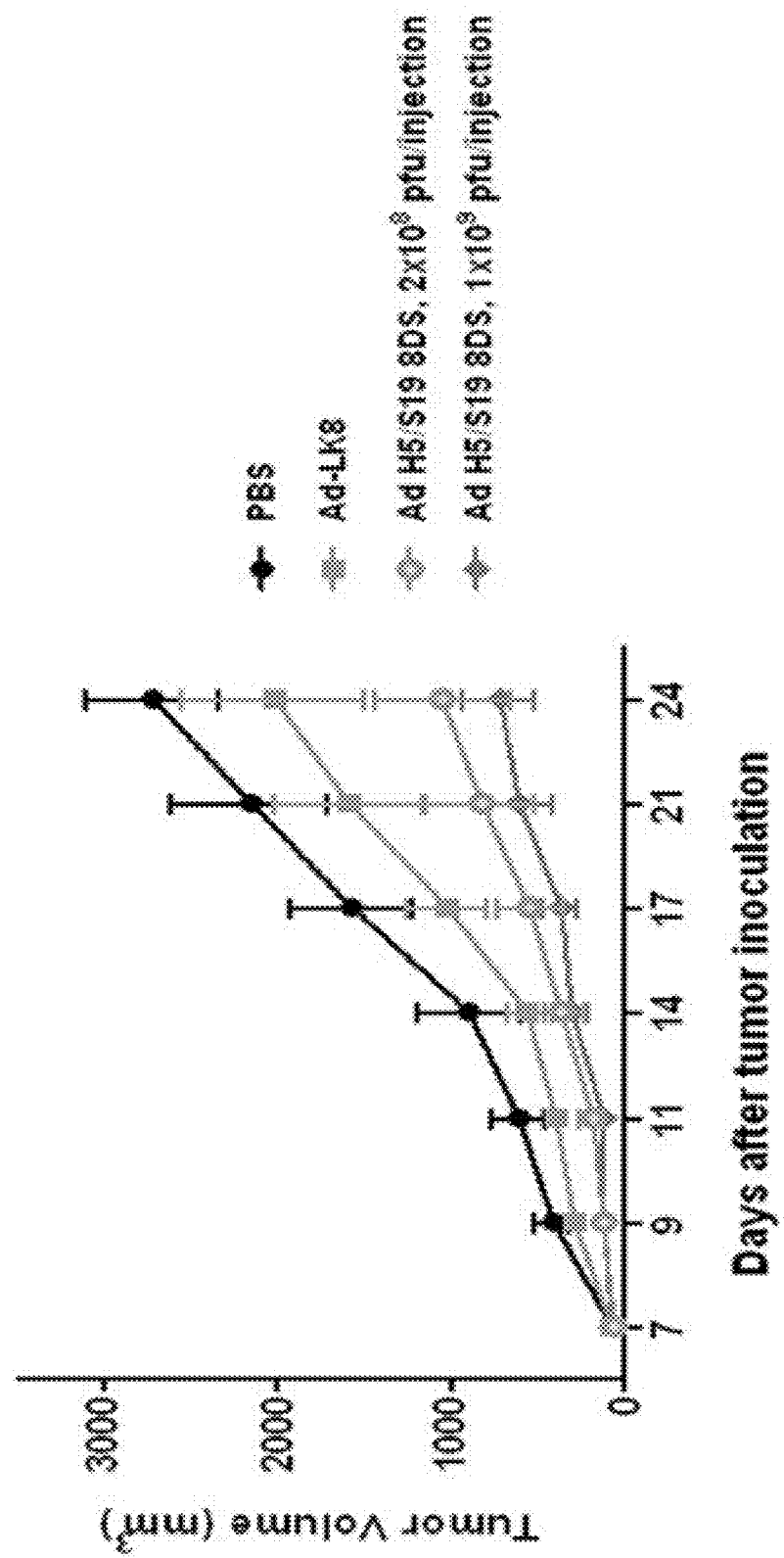

Tumor nodule score
0.5 cm ≥ 5
0.5~0.7 cm = 7
0.7~1.0 cm = 10

SEQUENCE LISTING

<160> NUMBER OF SEQ ID NOS: 27

<210> SEQ ID NO 1
<211> LENGTH: 26
<212> TYPE: DNA
<213> ORGANISM: Artificial Sequence
<220> FEATURE:
<223> OTHER INFORMATION: Hexon F primer (Mfe I)

<400> SEQUENCE: 1
ggcaattgat ggccacccca tcgatg                                    26

<210> SEQ ID NO 2
<211> LENGTH: 26
<212> TYPE: DNA
<213> ORGANISM: Artificial Sequence
<220> FEATURE:
<223> OTHER INFORMATION: Hexon R primer (Mfe I)

<400> SEQUENCE: 2
ggcaattgtt aggtggtggc gttgcc                                    26

<210> SEQ ID NO 3
<211> LENGTH: 2799
<212> TYPE: DNA
<213> ORGANISM: Simian Adenovirus Serotype 19

<400> SEQUENCE: 3

```
atggccaccc catcgatgat gccgcagtgg tcttacatgc acatcgccgg gcaggacgcc    60
tcggagtacc tgagccccgg cctcgtgcag tttgcccgcg ccaccgacac ctacttcagc   120
ttgggaaaca agtttagaaa ccccaccgtg gcccccacgc acgatgtgac cacggaccgc   180
tcgcagagac tgaccctgcg ctttgtgccc gtagaccggg aggacaccgc ttactcgtac   240
aaagtgcgct tcaccctagc agtaggggac aaccgtgtgt tggacatggc cagtaccaat   300
tttgacatcc ggggcacgct agaccgcggt cccagcttca agccttattc tggcacagct   360
tacaacgcgc tggcccctaa gggcgctccg aatgcttgtc agtggacaac cacgaatggg   420
ggtaacaaaa ctaattcatt tgctcaggcc ccagtaatcg gcctaagtat tgacgccacc   480
aacgggctaa aagtagggga ggagatacct gccactggag gggcaaatac gcccgtgtac   540
gccgacaaaa cattccagcc tgaacctcaa gtaggagaaa caaaatggaa ttctaacccc   600
actgagaatg cagctggaag aattttaaag ccaaacacac ctatgcagcc ctgctacgga   660
tcgtacgctc gaccaacaaa cgaaaaagga ggacaggcaa agctagttac taacggtcaa   720
gacaatcaaa aacgccaga cgttagttta aacttttta ctactgcgtc agaaaccaca   780
acattcacgc cgaaagttgt tctgtatagc gaaaacgtca acttggaagc tccagatacg   840
catctagtat acaagccaga cggcactgac ggaatcacca acgccgaaac tctcttagga   900
cttcagtcag ctccgaacag accaaattac attggttttc gagataactt tataggccta   960
atgtattaca actccactgg aaatatgggg gttctggccg acaggcttc gcaattaaac  1020
gcagtggttg atttgcaaga cagaaacaca gaattgtcat accaacttat gctggatgcc  1080
ctgggagacc gcagtaggta cttctccatg tggaatcagg ctgtggacag ctatgatcct  1140
gatgttagga taatagaaaa ccatggcgta gaagacgaat gcctaactta ctgctttcca  1200
cttaatgcgc aaggtgtagc caacacttac cagggcgtta aaaatggctc gggaaactgg  1260
tcgaaagaca ctaacgttgg cacggcaaat gaaatcggga taggtaacat ttttgctttc  1320
gaaattaatc tagctgccaa cttgtggcga agttttcttt actccaatgt ggccttgtac  1380
ctgcccgacg cttacaaatt aaccctgac aacattacgc ttccagacaa caaaaacacc  1440
tacgagtata taaacggccg cgtggctgcg cccgcctctc tagacaccta cgttaacatt  1500
ggagcgcgct ggtctcccga cccgatggat aacgttaacc cctttaacca tcaccgcaac  1560
gcgggttttgc gctatcgctc tatgctactg gcaacggcc gctacgttcc ttttcacata  1620
caagtgcccc aaaaattttt tgccattaaa aacctgctgc tccttccggg ctcctacacc  1680
tacgagtgga atttaggaa ggatgtaaac atgatttgc agagcacact tggtaacgac  1740
ctacggggttg acggggcgag cgttaggttt gatagcatca acctgtacgc aaattttttc  1800
cccatggcgc ataacacagc gtccacgctg gaagccatgc tgcgtaatga cacaaacgac  1860
cagtctttta acgactacct ctgcgccgcc aacatgcttt accctattcc ggccaatgcc  1920
actagtgttc caatttccat tccctctcgc aattgggcag ctttccgcgg ctggagcttc  1980
acgcgactta aaactcggga aacgccttcc cttggatctg gatttgaccc ttactttgtg  2040
tactccggtt ccatcccta cctggatggc acctttatc taaaccatac ttttaaaaag  2100
gtgtccatta tgttcgactc ctcagtaagc tggcctggca acgaccgcct cctgactcct  2160
aatgaattcg agattaagcg gtcggtggac ggagaaggct acaacgtggc ccaaagcaat  2220
atgacaaaag attggttttt aattcaaatg ttaagtcact acaacatcgg ttatcaggga  2280
```

-continued

| | |
|---|---|
| ttctacgttc cagaatccta caaggacaga atgtactctt ttttcagaaa cttccaacct | 2340 |
| atgagccgac aggtggtgga tcctgtaaat tacacaaact acaaggaagt tacattgccg | 2400 |
| tatcagcata ataattcagg cttttgtgggg tacatgggtc ctaccatgag agagggtcag | 2460 |
| gcctacccag ctaactaccc ttacccgcta ataggcaaaa cggcagtacc cagcctcacc | 2520 |
| cagaaaagt tcctgtgcga cagggtgatg tggagaattc ccttttctag caactttatg | 2580 |
| tctatggggg ctctgaccga cctggggcag aacatgctgt atgccaactc cgctcatgcc | 2640 |
| ttggacatga cttttgaggt ggatcccatg gatgagccca cgcttcttta tgttttgttc | 2700 |
| gaagtcttcg acgtggtgcg cattcaccag ccgcaccgcg gcgtcatcga ggccgtctac | 2760 |
| ctgcgcacgc ctttctctgc cggcaacgcc accacctaa | 2799 |

<210> SEQ ID NO 4
<211> LENGTH: 24
<212> TYPE: DNA
<213> ORGANISM: Artificial Sequence
<220> FEATURE:
<223> OTHER INFORMATION: HexonL F primer (XhoI)

<400> SEQUENCE: 4
ctcgaggtcg caccgtcgca tgcg                                      24

<210> SEQ ID NO 5
<211> LENGTH: 24
<212> TYPE: DNA
<213> ORGANISM: Artificial Sequence
<220> FEATURE:
<223> OTHER INFORMATION: HexonL R primer (EcoRI)

<400> SEQUENCE: 5
gaattccttg gaaagcgggc gcgc                                      24

<210> SEQ ID NO 6
<211> LENGTH: 24
<212> TYPE: DNA
<213> ORGANISM: Artificial Sequence
<220> FEATURE:
<223> OTHER INFORMATION: HexonR F primer (EcoRI)

<400> SEQUENCE: 6
gaattcagaa gcaagcaaca tcaa                                      24

<210> SEQ ID NO 7
<211> LENGTH: 24
<212> TYPE: DNA
<213> ORGANISM: Artificial Sequence
<220> FEATURE:
<223> OTHER INFORMATION: HexonR R primer (HindIII)

<400> SEQUENCE: 7
aagcttctga tagtgttcca gtgc                                      24

<210> SEQ ID NO 8
<211> LENGTH: 23
<212> TYPE: DNA
<213> ORGANISM: Artificial Sequence
<220> FEATURE:
<223> OTHER INFORMATION: DS promoter F primer

<400> SEQUENCE: 8
cttctcgctg ctttatcccc atc                                       23

```
<210> SEQ ID NO 9
<211> LENGTH: 21
<212> TYPE: DNA
<213> ORGANISM: Artificial Sequence
<220> FEATURE:
<223> OTHER INFORMATION: DS Promoter R primer

<400> SEQUENCE: 9
ctcggaggct tcagcagacg c                                              21

<210> SEQ ID NO 10
<211> LENGTH: 18
<212> TYPE: DNA
<213> ORGANISM: Artificial Sequence
<220> FEATURE:
<223> OTHER INFORMATION: Hexon HR F primer

<400> SEQUENCE: 10
atgcgcaagg tgtagcca                                                  18

<210> SEQ ID NO 11
<211> LENGTH: 18
<212> TYPE: DNA
<213> ORGANISM: Artificial Sequence
<220> FEATURE:
<223> OTHER INFORMATION: Hexon HR R primer

<400> SEQUENCE: 11
agcgtgctgg ccagcgtg                                                  18

<210> SEQ ID NO 12
<211> LENGTH: 18
<212> TYPE: DNA
<213> ORGANISM: Artificial Sequence
<220> FEATURE:
<223> OTHER INFORMATION: CMV sense primer

<400> SEQUENCE: 12
cccgttacat aacttacg                                                  18

<210> SEQ ID NO 13
<211> LENGTH: 22
<212> TYPE: DNA
<213> ORGANISM: Artificial Sequence
<220> FEATURE:
<223> OTHER INFORMATION: E1A antisense primer

<400> SEQUENCE: 13
ttatggcctg gggcgtttac ag                                             22

<210> SEQ ID NO 14
<211> LENGTH: 24
<212> TYPE: DNA
<213> ORGANISM: Artificial Sequence
<220> FEATURE:
<223> OTHER INFORMATION: E4 sense primer

<400> SEQUENCE: 14
actcgagcac gttgtgcatt gtca                                           24

<210> SEQ ID NO 15
<211> LENGTH: 24
<212> TYPE: DNA
<213> ORGANISM: Artificial Sequence
<220> FEATURE:
<223> OTHER INFORMATION: E4 antisense primer
```

```
<400> SEQUENCE: 15
tgtcgactag ttttcttaaa atgg                                          24

<210> SEQ ID NO 16
<211> LENGTH: 932
<212> TYPE: PRT
<213> ORGANISM: Artificial Sequence
<220> FEATURE:
<223> OTHER INFORMATION: synthetic construct of SAd19 Hexon
<220> FEATURE:
<221> NAME/KEY: SITE
<222> LOCATION: (128)..(441)
<223> OTHER INFORMATION: HVR region

<400> SEQUENCE: 16
```

Met Ala Thr Pro Ser Met Met Pro Gln Trp Ser Tyr Met His Ile Ala
 1               5                  10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Phe Thr Leu Ala Val Gly Asp Asn Arg Val Leu Asp Met
                85                  90                  95

Ala Ser Thr Tyr Phe Asp Ile Arg Gly Thr Leu Asp Arg Gly Pro Ser
           100                 105                 110

Phe Lys Pro Tyr Ser Gly Thr Ala Tyr Asn Ala Leu Ala Pro Lys Gly
       115                 120                 125

Ala Pro Asn Ala Cys Gln Trp Thr Thr Thr Asn Gly Gly Asn Lys Thr
   130                 135                 140

Asn Ser Phe Ala Gln Ala Pro Val Ile Gly Leu Ser Ile Asp Ala Thr
145                 150                 155                 160

Asn Gly Leu Lys Val Gly Glu Glu Ile Pro Ala Thr Gly Gly Ala Asn
                165                 170                 175

Thr Pro Val Tyr Ala Asp Lys Thr Phe Gln Pro Glu Pro Gln Val Gly
            180                 185                 190

Glu Thr Lys Trp Asn Ser Asn Pro Thr Glu Asn Ala Ala Gly Arg Ile
        195                 200                 205

Leu Lys Pro Asn Thr Pro Met Gln Pro Cys Tyr Gly Ser Tyr Ala Arg
    210                 215                 220

Pro Thr Asn Glu Lys Gly Gly Gln Ala Lys Leu Val Thr Asn Gly Gln
225                 230                 235                 240

Asp Asn Gln Thr Thr Pro Asp Val Ser Leu Asn Phe Phe Thr Thr Ala
                245                 250                 255

Ser Glu Thr Thr Thr Phe Thr Pro Lys Val Val Leu Tyr Ser Glu Asn
            260                 265                 270

Val Asn Leu Glu Ala Pro Asp Thr His Leu Val Tyr Lys Pro Asp Gly
        275                 280                 285

Thr Asp Gly Ile Thr Asn Ala Glu Thr Leu Leu Gly Leu Gln Ser Ala
    290                 295                 300

Pro Asn Arg Pro Asn Tyr Ile Gly Phe Arg Asp Asn Phe Ile Gly Leu
305                 310                 315                 320

Met Tyr Tyr Asn Ser Thr Gly Asn Met Gly Val Leu Ala Gly Gln Ala

```
            325                 330                 335
Ser Gln Leu Asn Ala Val Val Asp Leu Gln Asp Arg Asn Thr Glu Leu
            340                 345                 350

Ser Tyr Gln Leu Met Leu Asp Ala Leu Gly Asp Arg Ser Arg Tyr Phe
            355                 360                 365

Ser Met Trp Asn Gln Ala Val Asp Ser Tyr Asp Pro Asp Val Arg Ile
            370                 375                 380

Ile Glu Asn His Gly Val Glu Asp Glu Leu Pro Asn Tyr Cys Phe Pro
385                 390                 395                 400

Leu Asn Ala Gln Gly Val Ala Asn Thr Tyr Gln Gly Val Lys Asn Gly
                405                 410                 415

Ser Gly Asn Trp Ser Lys Asp Thr Asn Val Gly Thr Ala Asn Glu Ile
            420                 425                 430

Gly Ile Gly Asn Ile Phe Ala Phe Glu Ile Asn Leu Ala Ala Asn Leu
                435                 440                 445

Trp Arg Ser Phe Leu Tyr Ser Asn Val Ala Leu Tyr Leu Pro Asp Ala
            450                 455                 460

Tyr Lys Leu Thr Pro Asp Asn Ile Thr Leu Pro Asp Asn Lys Asn Thr
465                 470                 475                 480

Tyr Glu Tyr Ile Asn Gly Arg Val Ala Pro Ala Ser Leu Asp Thr
                485                 490                 495

Tyr Val Asn Ile Gly Ala Arg Trp Ser Pro Asp Pro Met Asp Asn Val
                500                 505                 510

Asn Pro Phe Asn His His Arg Asn Ala Gly Leu Arg Tyr Arg Ser Met
            515                 520                 525

Leu Leu Gly Asn Gly Arg Tyr Val Pro Phe His Ile Gln Val Pro Gln
            530                 535                 540

Lys Phe Phe Ala Ile Lys Asn Leu Leu Leu Leu Pro Gly Ser Tyr Thr
545                 550                 555                 560

Tyr Glu Trp Asn Phe Arg Lys Asp Val Asn Met Ile Leu Gln Ser Thr
                565                 570                 575

Leu Gly Asn Asp Leu Arg Val Asp Gly Ala Ser Val Arg Phe Asp Ser
            580                 585                 590

Ile Asn Leu Tyr Ala Asn Phe Phe Pro Met Ala His Asn Thr Ala Ser
                595                 600                 605

Thr Leu Glu Ala Met Leu Arg Asn Asp Thr Asn Asp Gln Ser Phe Asn
            610                 615                 620

Asp Tyr Leu Cys Ala Ala Asn Met Leu Tyr Pro Ile Pro Ala Asn Ala
625                 630                 635                 640

Thr Ser Val Pro Ile Ser Ile Pro Ser Arg Asn Trp Ala Ala Phe Arg
                645                 650                 655

Gly Trp Ser Phe Thr Arg Leu Lys Thr Arg Glu Thr Pro Ser Leu Gly
                660                 665                 670

Ser Gly Phe Asp Pro Tyr Phe Val Tyr Ser Gly Ser Ile Pro Tyr Leu
            675                 680                 685

Asp Gly Thr Phe Tyr Leu Asn His Thr Phe Lys Lys Val Ser Ile Met
            690                 695                 700

Phe Asp Ser Ser Val Ser Trp Pro Gly Asn Asp Arg Leu Leu Thr Pro
705                 710                 715                 720

Asn Glu Phe Glu Ile Lys Arg Ser Val Asp Gly Glu Gly Tyr Asn Val
                725                 730                 735

Ala Gln Ser Asn Met Thr Lys Asp Trp Phe Leu Ile Gln Met Leu Ser
            740                 745                 750
```

His Tyr Asn Ile Gly Tyr Gln Gly Phe Tyr Val Pro Glu Ser Tyr Lys
            755                 760                 765

Asp Arg Met Tyr Ser Phe Phe Arg Asn Phe Gln Pro Met Ser Arg Gln
770                 775                 780

Val Val Asp Pro Val Asn Tyr Thr Asn Tyr Lys Glu Val Thr Leu Pro
785                 790                 795                 800

Tyr Gln His Asn Asn Ser Gly Phe Val Gly Tyr Met Gly Pro Thr Met
            805                 810                 815

Arg Glu Gly Gln Ala Tyr Pro Ala Asn Tyr Pro Tyr Pro Leu Ile Gly
            820                 825                 830

Lys Thr Ala Val Pro Ser Leu Thr Gln Lys Lys Phe Leu Cys Asp Arg
            835                 840                 845

Val Met Trp Arg Ile Pro Phe Ser Ser Asn Phe Met Ser Met Gly Ala
850                 855                 860

Leu Thr Asp Leu Gly Gln Asn Met Leu Tyr Ala Asn Ser Ala His Ala
865                 870                 875                 880

Leu Asp Met Thr Phe Glu Val Asp Pro Met Asp Glu Pro Thr Leu Leu
            885                 890                 895

Tyr Val Leu Phe Glu Val Phe Asp Val Val Arg Ile His Gln Pro His
            900                 905                 910

Arg Gly Val Ile Glu Ala Val Tyr Leu Arg Thr Pro Phe Ser Ala Gly
            915                 920                 925

Asn Ala Thr Thr
    930

<210> SEQ ID NO 17
<211> LENGTH: 952
<212> TYPE: PRT
<213> ORGANISM: Artificial Sequence
<220> FEATURE:
<223> OTHER INFORMATION: Synthetic construct of HAd5 Hexon
<220> FEATURE:
<221> NAME/KEY: SITE
<222> LOCATION: (128)..(461)
<223> OTHER INFORMATION: HVR region

<400> SEQUENCE: 17

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
            85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln

```
            145                 150                 155                 160
Ala Glu Gln Gln Lys Thr His Val Phe Gly Gln Ala Pro Tyr Ser Gly
                165                 170                 175
Ile Asn Ile Thr Lys Glu Gly Ile Gln Ile Gly Val Glu Gly Gln Thr
                180                 185                 190
Pro Lys Tyr Ala Asp Lys Thr Phe Gln Pro Glu Pro Gln Ile Gly Glu
                195                 200                 205
Ser Gln Trp Tyr Glu Thr Glu Ile Asn His Ala Ala Gly Arg Val Leu
                210                 215                 220
Lys Lys Thr Thr Pro Met Lys Pro Cys Tyr Gly Ser Tyr Ala Lys Pro
225                 230                 235                 240
Thr Asn Glu Asn Gly Gly Gln Gly Ile Leu Val Lys Gln Gln Asn Gly
                245                 250                 255
Lys Leu Glu Ser Gln Val Glu Met Gln Phe Phe Ser Thr Thr Glu Ala
                260                 265                 270
Thr Ala Gly Asn Gly Asp Asn Leu Thr Pro Lys Val Val Leu Tyr Ser
                275                 280                 285
Glu Asp Val Asp Ile Glu Thr Pro Asp Thr His Ile Ser Tyr Met Pro
                290                 295                 300
Thr Ile Lys Glu Gly Asn Ser Arg Glu Leu Met Gly Gln Gln Ser Met
305                 310                 315                 320
Pro Asn Arg Pro Asn Tyr Ile Ala Phe Arg Asp Asn Phe Ile Gly Leu
                325                 330                 335
Met Tyr Tyr Asn Ser Thr Gly Asn Met Gly Val Leu Ala Gly Gln Ala
                340                 345                 350
Ser Gln Leu Asn Ala Val Val Asp Leu Gln Asp Arg Asn Thr Glu Leu
                355                 360                 365
Ser Tyr Gln Leu Leu Asp Ser Ile Gly Asp Arg Thr Arg Tyr Phe
                370                 375                 380
Ser Met Trp Asn Gln Ala Val Asp Ser Tyr Asp Pro Asp Val Arg Ile
385                 390                 395                 400
Ile Glu Asn His Gly Thr Glu Asp Glu Leu Pro Asn Tyr Cys Phe Pro
                405                 410                 415
Leu Gly Gly Val Ile Asn Thr Glu Thr Leu Thr Lys Val Lys Pro Lys
                420                 425                 430
Thr Gly Gln Glu Asn Gly Trp Glu Lys Asp Ala Thr Glu Phe Ser Asp
                435                 440                 445
Lys Asn Glu Ile Arg Val Gly Asn Asn Phe Ala Met Glu Ile Asn Leu
                450                 455                 460
Asn Ala Asn Leu Trp Arg Asn Phe Leu Tyr Ser Asn Ile Ala Leu Tyr
465                 470                 475                 480
Leu Pro Asp Lys Leu Lys Tyr Ser Pro Ser Asn Val Lys Ile Ser Asp
                485                 490                 495
Asn Pro Asn Thr Tyr Asp Tyr Met Asn Lys Arg Val Val Ala Pro Gly
                500                 505                 510
Leu Val Asp Cys Tyr Ile Asn Leu Gly Ala Arg Trp Ser Leu Asp Tyr
                515                 520                 525
Met Asp Asn Val Asn Pro Phe Asn His His Arg Asn Ala Gly Leu Arg
                530                 535                 540
Tyr Arg Ser Met Leu Leu Gly Asn Gly Arg Tyr Val Pro Phe His Ile
545                 550                 555                 560
Gln Val Pro Gln Lys Phe Phe Ala Ile Lys Asn Leu Leu Leu Leu Pro
                565                 570                 575
```

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
            595                 600                 605

Lys Phe Asp Ser Ile Cys Leu Tyr Ala Thr Phe Pro Met Ala His
610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
            645                 650                 655

Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
            675                 680                 685

Pro Ser Leu Gly Ser Gly Tyr Asp Pro Tyr Tyr Thr Tyr Ser Gly Ser
            690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
            725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
            755                 760                 765

Gln Met Leu Ala Asn Tyr Asn Ile Gly Tyr Gln Gly Phe Tyr Ile Pro
            770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
            805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
            835                 840                 845

Pro Leu Ile Gly Lys Thr Ala Val Asp Ser Ile Thr Gln Lys Lys Phe
            850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
            885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
            915                 920                 925

His Arg Pro His Arg Gly Val Ile Glu Thr Val Tyr Leu Arg Thr Pro
            930                 935                 940

Phe Ser Ala Gly Asn Ala Thr Thr
945                 950

<210> SEQ ID NO 18
<211> LENGTH: 925
<212> TYPE: PRT
<213> ORGANISM: Artificial Sequence
<220> FEATURE:

```
<223> OTHER INFORMATION: Synthetic construct of HAd41 Hexon
<220> FEATURE:
<221> NAME/KEY: SITE
<222> LOCATION: (128)..(434)
<223> OTHER INFORMATION: HVR region

<400> SEQUENCE: 18
```

Met Ala Thr Pro Ser Met Met Pro Gln Trp Ser Tyr Met His Ile Ala
 1               5                  10                  15

Gly Gln Asp Ala Ser Glu Tyr Leu Ser Pro Gly Leu Val Gln Phe Ala
             20                  25                  30

Arg Ala Thr Asp Thr Tyr Phe Ser Leu Gly Asn Lys Phe Arg Asn Pro
         35                  40                  45

Thr Val Ala Pro Thr His Asp Val Thr Thr Asp Arg Ser Gln Arg Leu
     50                  55                  60

Thr Leu Arg Phe Val Pro Val Asp Arg Glu Asp Thr Ala Tyr Ser Tyr
 65                  70                  75                  80

Lys Val Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Thr
        115                 120                 125

Ala Pro Asn Pro Cys Glu Trp Lys Asp Asn Asn Lys Ile Lys Val Arg
    130                 135                 140

Gly Gln Ala Pro Phe Ile Gly Thr Asn Ile Asn Lys Asp Asn Gly Ile
145                 150                 155                 160

Gln Ile Gly Thr Asp Thr Thr Asn Gln Pro Ile Tyr Ala Asp Lys Thr
                165                 170                 175

Tyr Gln Pro Glu Pro Gln Val Gly Gln Thr Gln Trp Asn Ser Glu Val
            180                 185                 190

Gly Ala Ala Gln Lys Val Ala Gly Arg Val Leu Lys Asp Thr Thr Pro
        195                 200                 205

Met Leu Pro Cys Tyr Gly Ser Tyr Ala Lys Pro Thr Asn Glu Lys Gly
    210                 215                 220

Gly Gln Ala Ser Leu Ile Thr Asn Gly Thr Asp Gln Thr Leu Thr Ser
225                 230                 235                 240

Asp Val Asn Leu Gln Phe Phe Ala Leu Pro Ser Thr Pro Asn Glu Pro
                245                 250                 255

Lys Ala Val Leu Tyr Ala Glu Asn Val Ser Ile Glu Ala Pro Asp Thr
            260                 265                 270

His Leu Val Tyr Lys Pro Asp Val Ala Gln Gly Thr Ile Ser Ser Ala
        275                 280                 285

Asp Leu Leu Thr Gln Gln Ala Pro Asn Arg Pro Asn Tyr Ile Gly
    290                 295                 300

Phe Arg Asp Asn Phe Ile Gly Leu Met Tyr Tyr Asn Ser Thr Gly Asn
305                 310                 315                 320

Met Gly Val Leu Ala Gly Gln Ala Ser Gln Leu Asn Ala Val Val Asp
                325                 330                 335

Leu Gln Asp Arg Asn Thr Glu Leu Ser Tyr Gln Leu Met Leu Asp Ala
            340                 345                 350

Leu Gly Asp Arg Ser Arg Tyr Phe Ser Met Trp Asn Gln Ala Val Asp
        355                 360                 365

Ser Tyr Asp Pro Asp Val Arg Ile Ile Glu Asn His Gly Val Glu Asp
    370                 375                 380

```
Glu Leu Pro Asn Tyr Cys Phe Pro Leu Gly Gly Ser Ala Ala Thr Asp
385                 390                 395                 400

Thr Tyr Ser Gly Ile Lys Ala Asn Gly Gln Thr Trp Thr Ala Asp Asp
            405                 410                 415

Asn Tyr Ala Asp Arg Gly Ala Glu Ile Glu Ser Gly Asn Ile Phe Ala
            420                 425                 430

Met Glu Ile Asn Leu Ala Ala Asn Leu Trp Arg Ser Phe Leu Tyr Ser
        435                 440                 445

Asn Val Ala Leu Tyr Leu Pro Asp Ser Tyr Lys Ile Thr Pro Asp Asn
    450                 455                 460

Ile Thr Leu Pro Glu Asn Lys Asn Thr Tyr Ala Tyr Met Asn Gly Arg
465                 470                 475                 480

Val Ala Val Pro Ser Ala Leu Asp Thr Tyr Val Asn Ile Gly Ala Arg
                485                 490                 495

Trp Ser Pro Asp Pro Met Asp Asn Val Asn Pro Phe Asn His His Arg
            500                 505                 510

Asn Ala Gly Leu Arg Tyr Arg Ser Met Leu Leu Gly Asn Gly Arg Tyr
        515                 520                 525

Val Pro Phe His Ile Gln Val Pro Gln Lys Phe Ala Ile Lys Asn
    530                 535                 540

Leu Leu Leu Leu Pro Gly Ser Tyr Thr Tyr Glu Trp Asn Phe Arg Lys
545                 550                 555                 560

Asp Val Asn Met Ile Leu Gln Ser Ser Leu Gly Asn Asp Leu Arg Val
                565                 570                 575

Asp Gly Ala Ser Val Arg Phe Asp Ser Ile Asn Leu Tyr Ala Asn Phe
            580                 585                 590

Phe Pro Met Ala His Asn Thr Ala Ser Thr Leu Glu Ala Met Leu Arg
        595                 600                 605

Asn Asp Thr Asn Asp Gln Ser Phe Asn Asp Tyr Leu Cys Ala Ala Asn
    610                 615                 620

Met Leu Tyr Pro Ile Pro Ser Asn Ala Thr Ser Val Pro Ile Ser Ile
625                 630                 635                 640

Pro Ser Arg Asn Trp Ala Ala Phe Arg Gly Trp Ser Phe Thr Arg Leu
                645                 650                 655

Lys Thr Lys Glu Thr Pro Ser Leu Gly Ser Gly Phe Asp Pro Tyr Phe
            660                 665                 670

Thr Tyr Ser Gly Ser Val Pro Tyr Leu Asp Gly Thr Phe Tyr Leu Asn
        675                 680                 685

His Thr Phe Lys Lys Val Ser Ile Met Phe Asp Ser Ser Val Ser Trp
    690                 695                 700

Pro Gly Asn Asp Arg Leu Leu Thr Pro Asn Glu Phe Glu Ile Lys Arg
705                 710                 715                 720

Thr Val Asp Gly Glu Gly Tyr Asn Val Ala Gln Cys Asn Met Thr Lys
                725                 730                 735

Asp Trp Phe Leu Ile Gln Met Leu Ser His Tyr Asn Ile Gly Tyr Gln
            740                 745                 750

Gly Phe Tyr Val Pro Glu Ser Tyr Lys Asp Arg Met Tyr Ser Phe Phe
        755                 760                 765

Arg Asn Phe Gln Pro Met Ser Arg Gln Val Val Asn Thr Thr Thr Tyr
    770                 775                 780

Lys Glu Tyr Gln Asn Val Thr Leu Pro Phe Gln His Asn Asn Ser Gly
785                 790                 795                 800
```

```
Phe Val Gly Tyr Met Gly Pro Thr Met Arg Glu Gly Gln Ala Tyr Pro
                805                 810                 815

Ala Asn Tyr Pro Tyr Pro Leu Ile Gly Gln Thr Ala Val Pro Ser Leu
            820                 825                 830

Thr Gln Lys Lys Phe Leu Cys Asp Arg Thr Met Trp Arg Ile Pro Phe
        835                 840                 845

Ser Ser Asn Phe Met Ser Met Gly Ala Leu Thr Asp Leu Gly Gln Asn
    850                 855                 860

Met Leu Tyr Ala Asn Ser Ala His Ala Leu Asp Met Thr Phe Glu Val
865                 870                 875                 880

Asp Pro Met Asp Glu Pro Thr Leu Leu Tyr Val Leu Phe Glu Val Phe
                885                 890                 895

Asp Val Val Arg Ile His Gln Pro His Arg Gly Val Ile Glu Ala Val
            900                 905                 910

Tyr Leu Arg Thr Pro Phe Ser Ala Gly Asn Ala Thr Thr
        915                 920                 925

<210> SEQ ID NO 19
<211> LENGTH: 942
<212> TYPE: DNA
<213> ORGANISM: Artificial Sequence
<220> FEATURE:
<223> OTHER INFORMATION: Sequence of hypervariable region of SAd19 Hexon

<400> SEQUENCE: 19
ggcgctccga atgcttgtca gtggacaacc acgaatgggg gtaacaaaac taattcattt      60
gctcaggccc cagtaatcgg cctaagtatt gacgccacca acgggctaaa agtaggggag     120
gagatacctg ccactggagg ggcaaatacg cccgtgtacg ccgacaaaac attccagcct     180
gaacctcaag taggagaaac aaaatggaat tctaacccta ctgagaatgc agctggaaga     240
attttaaagc caaacacacc tatgcagccc tgctacggat cgtacgctcg accaacaaac     300
gaaaaaggag acaggcaaa gctagttact aacggtcaag acaatcaaac aacgccagac     360
gttagtttaa acttttttac tactgcgtca gaaaccacaa cattcacgcc gaaagttgtt     420
ctgtatagcg aaaacgtcaa cttggaagct ccagatacgc atctagtata caagccagac     480
ggcactgacg gaatcaccaa cgccgaaact ctcttaggac ttcagtcagc tccgaacaga     540
ccaaattaca ttggttttcg agataacttt ataggcctaa tgtattacaa ctccactgga     600
aatatggggg ttctggccgg acaggcttcg caattaaacg cagtggttga tttgcaagac     660
agaaacacag aattgtcata ccaacttatg ctggatgccc tgggagaccg cagtaggtac     720
ttctccatgt ggaatcaggc tgtggacagc tatgatcctg atgttaggat aatagaaaac     780
catggcgtag aagacgaatt gcctaactac tgctttccac ttaatgcgca aggtgtagcc     840
aacacttacc agggcgttaa aaatggctcg ggaaactggt cgaaagacac taacgttggc     900
acggcaaatg aaatcgggat aggtaacatt tttgctttcg aa                       942

<210> SEQ ID NO 20
<211> LENGTH: 314
<212> TYPE: PRT
<213> ORGANISM: Artificial Sequence
<220> FEATURE:
<223> OTHER INFORMATION: Sequence of hypervariable region of SAd19 Hexon

<400> SEQUENCE: 20

Gly Ala Pro Asn Ala Cys Gln Trp Thr Thr Thr Asn Gly Gly Asn Lys
1               5                   10                  15
```

```
Thr Asn Ser Phe Ala Gln Ala Pro Val Ile Gly Leu Ser Ile Asp Ala
             20                  25                  30

Thr Asn Gly Leu Lys Val Gly Glu Glu Ile Pro Ala Thr Gly Gly Ala
         35                  40                  45

Asn Thr Pro Val Tyr Ala Asp Lys Thr Phe Gln Pro Glu Pro Gln Val
     50                  55                  60

Gly Glu Thr Lys Trp Asn Ser Asn Pro Thr Glu Asn Ala Ala Gly Arg
 65                  70                  75                  80

Ile Leu Lys Pro Asn Thr Pro Met Gln Pro Cys Tyr Gly Ser Tyr Ala
                 85                  90                  95

Arg Pro Thr Asn Glu Lys Gly Gly Gln Ala Lys Leu Val Thr Asn Gly
            100                 105                 110

Gln Asp Asn Gln Thr Thr Pro Asp Val Ser Leu Asn Phe Phe Thr Thr
        115                 120                 125

Ala Ser Glu Thr Thr Thr Phe Thr Pro Lys Val Val Leu Tyr Ser Glu
    130                 135                 140

Asn Val Asn Leu Glu Ala Pro Asp Thr His Leu Val Tyr Lys Pro Asp
145                 150                 155                 160

Gly Thr Asp Gly Ile Thr Asn Ala Glu Thr Leu Leu Gly Leu Gln Ser
                165                 170                 175

Ala Pro Asn Arg Pro Asn Tyr Ile Gly Phe Arg Asp Asn Phe Ile Gly
            180                 185                 190

Leu Met Tyr Tyr Asn Ser Thr Gly Asn Met Gly Val Leu Ala Gly Gln
        195                 200                 205

Ala Ser Gln Leu Asn Ala Val Val Asp Leu Gln Asp Arg Asn Thr Glu
    210                 215                 220

Leu Ser Tyr Gln Leu Met Leu Asp Ala Leu Gly Asp Arg Ser Arg Tyr
225                 230                 235                 240

Phe Ser Met Trp Asn Gln Ala Val Asp Ser Tyr Asp Pro Asp Val Arg
                245                 250                 255

Ile Ile Glu Asn His Gly Val Glu Asp Glu Leu Pro Asn Tyr Cys Phe
            260                 265                 270

Pro Leu Asn Ala Gln Gly Val Ala Asn Thr Tyr Gln Gly Val Lys Asn
        275                 280                 285

Gly Ser Gly Asn Trp Ser Lys Asp Thr Asn Val Gly Thr Ala Asn Glu
    290                 295                 300

Ile Gly Ile Gly Asn Ile Phe Ala Phe Glu
305                 310

<210> SEQ ID NO 21
<211> LENGTH: 31
<212> TYPE: PRT
<213> ORGANISM: Artificial Sequence
<220> FEATURE:
<223> OTHER INFORMATION: Synthetic construct, Highly variable Region
      (HVR)-1, corresponding to amino acid residues 138-168 of SEQ ID
      NO: 16 and amino acid residues 11-41 of SEQ ID NO: 20

<400> SEQUENCE: 21

Thr Asn Gly Gly Asn Lys Thr Asn Ser Phe Ala Gln Ala Pro Val Ile
  1               5                  10                  15

Gly Leu Ser Ile Asp Ala Thr Asn Gly Leu Lys Val Gly Glu Glu
             20                  25                  30

<210> SEQ ID NO 22
<211> LENGTH: 7
<212> TYPE: PRT
```

-continued

```
<213> ORGANISM: Artificial Sequence
<220> FEATURE:
<223> OTHER INFORMATION: Synthetic construct, Highly variable Region
      (HVR)-2, corresponding to amino acid residues 173-179 of SEQ ID
      NO: 16 and amino acid residues 46-52 of SEQ ID NO: 20

<400> SEQUENCE: 22

Gly Gly Ala Asn Thr Pro Val
 1               5

<210> SEQ ID NO 23
<211> LENGTH: 10
<212> TYPE: PRT
<213> ORGANISM: Artificial Sequence
<220> FEATURE:
<223> OTHER INFORMATION: Synthetic construct, Highly variable Region
      (HVR)-3, corresponding to amino acid residues 196-205 of SEQ ID
      NO: 16 and amino acid residues 69-78 of SEQ ID NO: 20

<400> SEQUENCE: 23

Trp Asn Ser Asn Pro Thr Glu Asn Ala Ala
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Synthetic construct, Highly variable Region
      (HVR)-4, corresponding to amino acid residues 106-119 of SEQ ID
      NO: 16 and amino acid residues 106-119 of SEQ ID NO: 20

<400> SEQUENCE: 24

Ala Lys Leu Val Thr Asn Gly Gln Asp Asn Gln Thr Thr Pro
 1               5                  10

<210> SEQ ID NO 25
<211> LENGTH: 13
<212> TYPE: PRT
<213> ORGANISM: Artificial Sequence
<220> FEATURE:
<223> OTHER INFORMATION: Synthetic construct, Highly variable Region
      (HVR)-5, corresponding to amino acid residues 126-138 of SEQ ID
      NO: 16 and amino acid residues 126-138 of SEQ ID NO: 20

<400> SEQUENCE: 25

Phe Thr Thr Ala Ser Glu Thr Thr Thr Phe Thr Pro Lys
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Synthetic construct, Highly variable Region
      (HVR)-6, corresponding to amino acid residues 287-300 of SEQ ID
      NO: 16 and amino acid residues 160-173 of SEQ ID NO: 20

<400> SEQUENCE: 26

Asp Gly Thr Asp Gly Ile Thr Asn Ala Glu Thr Leu Leu Gly
 1               5                  10

<210> SEQ ID NO 27
<211> LENGTH: 29
<212> TYPE: PRT
<213> ORGANISM: Artificial Sequence
<220> FEATURE:
<223> OTHER INFORMATION: Synthetic construct, Highly variable Region
      (HVR)-7, corresponding to amino acid residues 402-430 of SEQ ID
```

NO: 16 and amino acid residues 275-303 of SEQ ID NO: 20

<400> SEQUENCE: 27

Asn Ala Gln Gly Val Ala Asn Thr Tyr Gln Gly Val Lys Asn Gly Ser
1               5                   10                  15

Gly Asn Trp Ser Lys Asp Thr Asn Val Gly Thr Ala Asn
            20                  25

HEXON ISOLATED FROM SIMIAN ADENOVIRUS SEROTYPE 19, HYPERVARIABLE REGION THEREOF AND CHIMERIC ADENOVIRUS USING THE SAME

The present application is a divisional of U.S. application Ser. No. 13/641,027 filed Nov. 12, 2012, now abandoned, which is a National Stage of International Application No. PCT/KR2010/002298, filed on Apr. 14, 2010, the contents of which are herein incorporated by reference in their entirety.

FIELD OF THE INVENTION

The present invention relates to novel hexon isolated from simian adenovirus serotype 19 ("SAd19"), hypervariable region ("HVR") thereof, chimeric adenovirus using the same, and a therapeutic use thereof.

BACKGROUND OF THE INVENTION

Adenovirus belongs to the family Adenoviridae first isolated in 1953. Human adenoviruses are categorized into six (6) subgenera (A through F) based on the genome similarity, oncogenecity, and blood coagulation characteristics. Adenoviruses infect most non-divided cells such as muscle, lung, brain, and cardiac cells, and its molecular biological characteristics are well known in the art. Its genome is composed of a linear, double-stranded DNA of 35 kb and its replication in the host cell depends on viral protein, E1A.

Above characteristics of adenovirus can be exploited by using a nonreplicative vector having E1A deleted therefrom. Since the development of HEK293 cell line in which the adenoviral E1 gene is inserted, the adenovirus vector system has been used in numerous studies, which has led to the development of virotherapeutics that utilize cytotoxicity of the host cell. Oncorine®, which is the oncolytic virotherapeutics commercialized in China in 2005, is an E1B55-defective adenovirus for selectively inducing apoptotic cell death in p53-defective tumor.

In the development of selective replicative adenovirus therapeutic agents, selective expression of E1A protein is most important, and there have been suggested many cases regarding possible tumor-selective adenovirus gene therapeutic agents using tumor selective expression promoter. Most of the tumor-selective adenoviruses are prepared using the commonly-found human adenovirus serotype 5 ("HAd5"). It has been reported that human has high levels of adenovirus neutralizing antibodies, since HAd5 occupies 80% of prevalence (Appaiahgari, M. B., et al. (2007) *Clinical and Vaccine Immunol.* 14, 1053-1055). These neutralizing antibodies against adenoviral capsid protein influence the efficacy and toxicity of the adenovirus systemically administered (Chen, Y., et al. (2000) *Hum. Gene Ther* 11, 1553-1567).

Viral capsid consists of three (3) kinds of proteins, i.e., hexon, fiber, and penton, and comprises a capsomere having a symmetric icosahedron structure consisting of 240 hexons and 12 pentons. Each penton binds a protruded trimeric fiber of 70-100 nm. When infected by adenovirus, the trimeric fiber attaches to Coxackie Adenovirus Receptor (CAR) on the surface membrane of host cell in the process of adenovirus infection. The RGD region of penton binds to integrin, which leads to viral absorption and penetration into the host cell.

It has been reported that Loop 1 (L1) and Loop 2 (L2) of a hexon protein are exposed on the outside of the viral capsomere structure. L1 and L2 respectively contain six (6) hypervariable regions (HVRs), i.e., HVR-1 to HVR-6 within the $132^{nd}$ to $320^{th}$ amino acids and seventh HVR (HVR-7) within the $408^{th}$ to $459^{th}$ amino acids of the hexon protein.

The adenoviruses provide an elegant and efficient means of transferring therapeutic genes into cells. However, one problem encountered with the use of adenoviral vectors for gene transfer in vivo is the generation of antibodies to antigenic epitopes on adenoviral capsid proteins.

When adenovirus is administered to human body, neutralizing antibodies against hexon proteins are formed, and such antibodies mostly target the dominant HVR regions. It is also known that the antibodies reduce the efficiency of viral replication by way of inhibiting the infection of host cells (Wohlfart, C. (1988) *J. Virol.* 62, 2321-2328, Toogood, C. I. A., et al. (1992) *J. Gen. Virol.* 73, 1429-1435. Sumida, S. M., et al. (2005) *J. Immunol.* 174, 7179-7185).

The problems caused by the preponderance of human neutralizing antibodies against HAd5 in human must be overcome when administering adenovirus using a viral gene delivery vector and viral therapeutic agent. In addition to the above mentioned problems associated with the neutralizing antibodies, it has been reported that adenoviruses infect the liver when exposing systemically. In this connection, adenovirus has been reported to have hepatotropism, and when adenoviruses are administered via an intravenous route, 90% thereof is transferred to the liver within 24 hours (Worgall, S., et al. (1997) *Hum. Gene Ther* 8, 37-44). Due to such hepatoselectivity of the adenovirus, in 1999, young patient, Jessie Gelsinger, under a clinical trial using gene therapeutic adenovirus agents succumbed due to acute hepatotoxicity. Thus, dose of adenovirus has been restricted to an amount that does not exceed $1\times10^{13}$ vp since then. Therefore, hepatotoxicity is generally considered as a dose-limiting factor in nonclinical/clinical trials for many gene therapeutic agents using adenovirus (Alemany, R. et al. (2001) *Gene Ther,* 8(17), 1347-1353; Christ, M., et al. (2000) *Hum. Gene Ther.,* 11(3), 415-427; Lieber, A., et al. (1997) *J. Virol.,* 7(11), 8798-8807). Such liver selectivity is a major problem in achieving efficient cure by systemic administration of an adenoviral therapeutic agent (Worgall, S., et al. (1997) *Hum. Gene Ther,* 8, 37-44).

In this regard, Waddington et al. have recently reported that Gla domain, blood coagulating factor, combines with hexon protein of adenovirus in blood, which facilitates adenovirus transfer to the liver (Waddington, S. N., et al. (2008) *Cell,* 132, 397-409). It has been speculated that HVR-3, HVR-5 or HVR-7 of hexon can combine with blood coagulating factor, Gla domain (Kalyuzhniy, O., et al. (2008) *Proc. Nat'l Acd. Sci.* 105, 5483-5488). The HVR varies depending on the serotype of adenovirus, and it is not clear yet what is the crucial factor for binding affinity to blood coagulating factor. It has been reported that the maximum tolerated dose of adenovirus can be raised tenfold by way of inserting a specific protein such as RGD, RFP, and BAP (Biotin Acceptor Peptide) to significantly weaken binding affinity to blood coagulating factor and to reduce the hepatotropism (Shashkova, E. V., et al. (2009) *Mol. Ther.* 17, 2121-2130).

A number of functions of the hexon protein are now known, and many studies to modify hexon proteins in order to overcome the problems of hepatotoxicity and anti-adenoviral immunity are currently being conducted. There are four strategies for modifying hexon protein: 1) replacing the hexon gene with the corresponding hexon gene of other adenovirus serotype, 2) inserting a peptide into HVR, 3) replacing the gene encoding HVR of a hexon protein with the corresponding gene encoding HVR of other adenovirus serotype, and 4) removing the region from the HVR that binds the blood coagulating factor and neutralizing antibody. Up to date, the method of inserting a peptide into the HVR and the method of replacing the gene encoding HVR with the corresponding gene encoding HVR of other adenovirus serotype are carried out for hexon modification. Among above mentioned four strategies, complete hexon substitution is most apparent method to change viral immunogenicity. However, a method to achieve complete hexon exchange for modifying hexon protein has the problem of deteriorated productivity due to the fact that subtle structural differences in binding hexon to penton and fiber induce instability of the adenoviral capsid structure (Roberts, D. M., et al. (2006) *Nature*, 441, p 239-243; Youil, R., et al. (2002) *Hum. Gene. Ther.* 13, p 311-320; Shashkova, E., et al. (2009) *Mol. Ther* 17, 2121-2130).

Further, intense studies for the modification of capsid protein using serotypes of heterogenous adenovirus as well as those of human adenovirus are in progress. It has been reported that the prevalence rate of neutralizing antibodies against chimpanzee adenoviruses pan 5, 6, 7 and 9, classified as simian adenovirus serotypes 22 to 25, respectively, is less than 6%, and therefore, a simian adenoviral vector system including chimpanzee adenovirus can be useful as a gene therapeutic vector (Roy, S. et al. (2004) *Hum. Gene Ther* 15, p 519-530). International Patent Publication Nos. WO 2006/040330 and WO 2002/083902 teach the use of the fiber or hexon protein of human serotypes 11, 24, 26, 30, 34, 35, 48, 49, and 50 for suppressing immune response caused by neutralizing antibodies in the recombinant chimeric adenovirus where the adenoviral knob domain binding to the CAR or a hexon protein is substituted with those of other serotypes. Regarding simian adenovirus serotype, International Publication No. WO 2005/001103 discloses a chimeric adenovirus using simian adenovirus serotype 18.

However, there exists a strong need to develop an adenovirus having lower immunogenicity and lower toxicity. Thus, the present inventors have identified a novel SAd19 hexon gene isolated from baboon excrements and have found that it is highly capable of evading the neutralizing antibodies against HAd5 and it exhibits a low toxicity.

SUMMARY OF THE INVENTION

Accordingly, it is an object of the present invention to provide a novel hexon protein and a DNA encoding the same for use in the preparation of a chimeric adenovirus.

It is another object of the present invention to provide a chimeric adenovirus comprising the novel hexon protein.

It is a further object of the present invention to provide a composition comprising the chimeric adenovirus.

It is a still further object of the present invention to provide a method of gene therapy employing the chimeric adenovirus.

In accordance with one aspect of the present invention, there is provided a hexon isolated from SAd19 and a DNA encoding the hexon.

In accordance with another aspect of the present invention, there is provided a HVR of the hexon isolated from SAd19 and a DNA encoding the HVR.

In accordance with a further aspect of the present invention, there is provided a chimeric adenovirus having a nonnative amino acid sequence in the hexon by the substitution of the hexon protein isolated from SAd19, or seven (7) or more consecutive residues therefrom.

In accordance with a still further aspect of the present invention, there is provided a composition comprising the chimeric adenovirus of the present invention.

In accordance with a still further aspect of the present invention, there is provided a method for delivering a therapeutic transgene to a mammalian cell comprising introducing into said cell the chimeric adenovirus of the present invention.

In accordance with a still further aspect of the present invention, there is provided a method for treating cancers comprising administering into a subject the chimeric adenovirus of the present invention.

In accordance with a still further aspect of the present invention, there is provided a method for preparing an adenoviral vector for gene therapy comprising substituting seven (7) or more amino acid residues in the hexon of a human adenovirus with seven (7) or more residues of the hexon protein of the present invention.

In accordance with a still further aspect of the present invention, there is provided an isolated host cell comprising the chimeric adenovirus of the present invention.

BRIEF DESCRIPTION OF THE DRAWINGS

The above and other objects and features of the present invention will become apparent from the following description of the invention, when taken in conjunction with the accompanying drawings, which respectively show:

FIG. 1A: amino acid sequences of hexon proteins from human adenovirus (HAd) serotypes 5 and SAd19;

FIG. 1B: amino acid sequences of hexon proteins from human adenovirus (HAd) serotypes 41 and SAd19;

FIG. 7(A): an immunostaining photograph showing the infection-evading ability of chimeric adenoviruses having hexon of SAd19, Ad H5/S19_8DS, by employing neutralizing antibodies against HAd5;

FIG. 7(B): a bar graph showing the infection-evading ability of chimeric adenoviruses having hexon of SAd19, Ad H5/S19_8DS, by employing neutralizing antibodies against HAd5;

FIG. 7(C): an immunostaining photograph showing the infection-evading ability of chimeric adenoviruses having hexon of Ad328 H5/S19_DS and Ad328 H5/S19_DS Δ19k, by employing neutralizing antibodies against HAd5;

FIG. 8: a graph showing the expression pattern of LK8 gene in blood transferred by Ad H5/S19_8DS and Ad H5_8DS which are administered to Syrian hamster immunized by HAd5;

FIGS. 10(A) and 10(B): blood analysis data of the mice into which Ad H5_8DS is intravenously administered;

FIGS. 11(A) and 11(B): blood analysis data of the mice into which Ad H5/S19_8DS is intravenously administered;

FIG. 12: a tumor-growth curve in the animal model for H460 non-small cell lung cancer after intravenous injection of Ad H5/S19_8DS;

DETAILED DESCRIPTION OF THE INVENTION

Figure 2A:
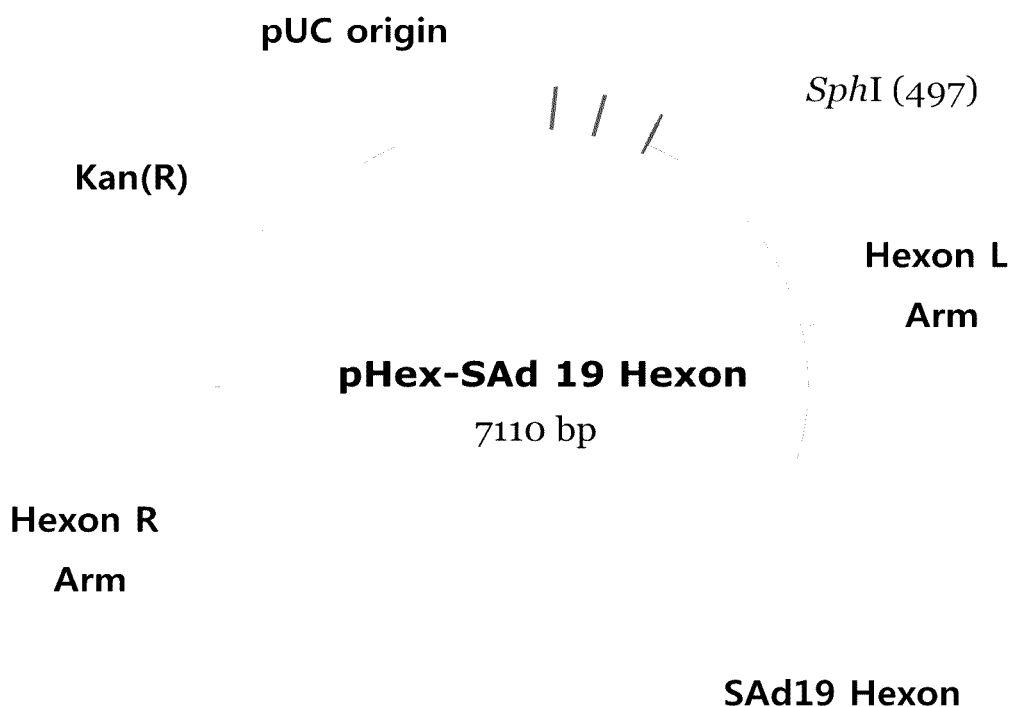
FIG. 2A: cleavage maps of pHex-SAd19 Hexon vector.

Unless defined otherwise, technical and scientific terms used herein have the same meaning as commonly understood by one of ordinary skill in the art to which the invention belongs. Further, all documents mentioned herein are incorporated by reference in their entireties.

The term "adenovirus" as used herein refers to a non-enveloped icosahedral double-stranded DNA virus having about a linear genome of about 36 kb.

The term "chimeric adenovirus" as used herein refers to an adenovirus whose nucleic acid sequence is comprised of the nucleic acid sequences of at least two of the adenoviral serotypes.

As used herein, "substitution" results from the replacement of one or more polynucleotides or amino acids by different polynulceotides or amino acids, respectively.

The term "hypervariable region" or "HVR" as used herein means a variable domain, whose sequence is hypervariable, forming structurally limited loop.

The term "nonnative amino acid sequence" as used herein means any amino acid sequence that is not found in the native hexon protein of a given serotype of adenovirus, and is introduced into the hexon protein at the level of gene expression (i.e., by production of a nucleic acid sequence that encodes the nonnative amino acid sequence).

The term "therapeutic transgene" as used herein refers to a polynucleotide that is introduced into a cell and is capable of being translated and/or expressed under appropriate conditions and confers a desired property to a cell into which it was introduced, or otherwise leads to a desired therapeutic outcome.

The term "vector" as used herein refers to a vehicle for gene transfer as that term is understood by those skilled in the art, and includes viruses, plasmids, and the like.

The term "neutralizing antibody" as used herein means an antibody being able to inhibit infectivity of (i.e., cell entry) or gene expression commanded by an adenovirus. The neutralizing antibody may be an antibody that either is purified from or is present in serum.

The present invention is described in detail hereinafter.

In the present invention, there is provided a hexon isolated from SAd19, a HVR thereof and DNAs encoding the hexon.

The SAd19 according to the present invention may be provided by the isolation from the baboon excrements and is classified as subgroup F. The hexon of SAd19 has an amino acid sequence of SEQ ID NO: 16, which has 85% homology with that of the human adenovirus serotype 41 ("HAd41") hexon and 76% homology with that of HAd5 hexon. Further, the nucleotide sequence encoding the hexon of SAd19 has 76% homology with that of the HAd41 hexon and 70% homology with that of the HAd5 hexon. Preferably, the hexon of SAd19 according to the present invention has the DNA sequence of SEQ ID NO: 3.

The hexon of SAd19 or seven (7) or more residues therefrom may be incorporated into various types of adenoviruses by the substitution in order to provide a chimeric adenovirus. Accordingly, there is provided a chimeric adenovirus having a nonnative amino acid sequence in the hexon by the substitution of the hexon protein of SAd19 of the present invention, or one or more residues therefrom.

Preferably, the chimeric adenovirus may have a nonnative amino acid sequence in the hexon by the substitution of seven (7) or more residues from the hexon having the amino acid sequence of SEQ ID NO: 16. The seven (7) or more residues from the hexon of SAd19 may be HVR. The HVR may have the amino acid sequence of SEQ ID NO: 20 and may be encoded by the nucleotide sequence of SEQ ID NO: 19. More preferably, the chimeric adenovirus may have a nonnative amino acid sequence in the hexon by the substitution of the fragment of the HVR, i.e., HVR-1 to -7, which correspond to the amino acid residues 11 to 41, 46 to 52, 69 to 78, 106 to 119, 126 to 138, 160 to 173, and 275 to 303 of SEQ ID NO: 20, respectively. The peptides of these residues are shown as SEQ ID NO: 21, SEQ ID NO: 22, SEQ ID NO: 23, SEQ ID NO: 24, SEQ ID NO: 25, SEQ ID NO: 26, and SEQ ID NO: 27, respectively.

The chimeric adenovirus having the hexon of SAd19 or seven (7) or more residues therefrom shows little immune inhibition by neutralizing antibodies and hepatotoxicity.

Various types of the adenovirus, preferably human adenovirus serotype, more preferably, human adenovirus serotypes 5, 11, 24, 26, 30, 34, 35, 48, 49, and 50 may be useful for the preparation of the present chimeric adenovirus. Tumor-specific, replication-competent adenovirus or tumor-specific, replication-restricted adenovirus may be useful as the adenovirus therapeutic agent. The chimeric adenovirus of the present invention has a nonnative amino acid sequence so as to overcome problems of immune response and hepatotoxicity.

In particular, the nonnative amino acid sequence according to the present invention is prepared by substituting a hexon region of a wild-type adenovirus with that of SAd19. Optimally the resultant nonnative amino acid sequence is such that seven (7) or more of the existing epitopes for neutralizing antibodies directed against the corresponding wild-type adenovirus hexon protein have been rendered non-immunogenic.

According to the present invention, the chimeric adenovirus comprises hexon modification of seven (7) or more amino acids, and such hexon modification is made in seven (7) or more regions.

The most preferable chimeric adenovirus may be Ad H5/S19_8DS, which is prepared by transduction of the adenoviral vector pAd H5/S19_8DS into human lung adenocarcinoma epithelial cell line, A549, thereby substituting human adenoviral hexon with the hexon of SAd19.

In a preferred embodiment of the present invention, the chimeric adenovirus of the present invention may further contain therapeutic transgene. The non-limiting examples of such therapeutic transgene include tumor suppressor gene, antigenic gene, cytotoxic gene, cytostatic gene, suicide gene, anti-angiogenic gene and immune-modulatory gene.

Concretely, the "tumor suppressor gene" is a nucleotide sequence, the expression of which in the target cell is capable of suppressing the neoplastic phenotype and/or inducing apoptosis. Examples of the tumor suppressor gene include p53-gene, APC-gene, DPC-4/Smad4 gene, BRCA-1 gene, BRCA-2 gene, WT-1 gene, retinoblastoma gene (Lee et al., *Nature,* 1987, 329,642), MMAC-1 gene, adenomatous polyposis coil protein (U.S. Pat. No. 5,783,666), DCC (deleted in colorectal cancer) gene, MMSC-2 gene, nasopharyngeal cancer suppressor gene located on chromosome 3p21.3 (Cheng et al., Proc. Nat. Acad. Sci., 1998, 95, 3042-3047), MTS1 gene, CDK4 gene, NF-1 gene, NF-2 gene, VHL gene, etc.

The "antigenic gene" is a nucleotide sequence, the expression of which in the target cells results in the production of a cell surface antigenic protein capable of recognition by the immune system. In the example of this antigenic gene, the carcinoembryonic antigen (CEA), CD3, CD133, CD44, and p53 (International Publication No. WO94/02167) are included. For easy recognition of the immune system, the antigenic gene may be combined with the MHC type I antigen.

The "cytotoxic gene" is a nucleotide sequence exhibiting the toxic effect when expressed in cells. Examples of the cytotoxic gene include nucleotide sequences coding *Pseudomonas* exotoxin, ricin toxin, diphtheria toxin, etc.

The "cytostatic gene" is a nucleotide sequence inducing cell cycle arrest when expressed in cells. The non-limiting examples of the cytostatic gene include p21, retinoblastoma gene, E2F-Rb fusion protein gene, genes coding cyclin-dependent kinase inhibitor (for example, p16, p15, p18, and p19), growth arrest specific homeobox (GAX) gene (International Patent Publication Nos. WO97/16459 and WO 96/30385), etc.

The "suicide gene" is a nucleotide sequence inducing cell death through apoptosis when expressed in the cell. The non-limiting examples of the suicide gene encompasses genes coding herpes simplex virus thymidine kinase, varicella thymidine kinase, cytosine deaminase, purine nucleoside phosphorylase, beta-lactanase, carboxypeptidase G2, cytochrome P450-2B1, nitroreductase, beta-glucuronidase, TRAIL (TNF related apoptosis-inducing ligand), etc.

The "anti-angiogenic gene" is a nucleotide sequence, the expression of which results in the extracellular secretion of anti-angiogenic factors. The anti-angiogenic factor encompasses angiostatin, inhibitor of vascular endothelial growth factor (VEGF) and placental growth factor (PlGF) such as soluble VEGFR1 (sFLT-1) (PNAS (USA), 1998, 95, 8795-800), endostatin, and apolipoprotein(a) kringle domain (LK8). The preferred anti-angiogenic gene is a gene encoding LK8. LK8 directly influence the vascular endothelial cell to induce apoptosis and inhibit the migration of the epithelial cell (Kim J S et al., *J. Biol. Chem.,* (2003) 278:29000). In particular, it has been reported that adenovirus-mediated expression of LK8 suppresses hepatocellular carcinoma growth in mice (Lee K. et al., *Hepatology* (2006) 43:1063). Therefore, it is expected that oncolytic effect of adenovirus may be improved by the introduction of LK8.

The "immune-modulatory gene" is a nucleotide sequence, which modulates humoral and cellular immune response, when expressed in the cell. The non-limiting examples of the immno-modulatory gene encompass genes coding CD16, CTLA-4, IL24, GM-CSF, etc.

The therapeutic transgene may be inserted into the inventive chimeric adenovirus by various DNA recombinant technologies known in the art.

The present invention also provides the use of the inventive chimeric adenoviruses for the inhibition of tumor cell growth, as well as for the preparation of adenoviral vectors to deliver therapeutic transgene useful in the treatment of tumor and other disease. Specifically, there are provided a method for delivering a therapeutic transgene to mammalian cell comprising introducing said cell the chimeric adenovirus of the present invention; a method for treating cancers comprising administering said adenovirus into a subject; and a method for preparing an adenoviral vector for gene therapy comprising substituting seven (7) or more amino acid residues in the hexon of a human adenovirus with seven (7) or more residues of the SAd19 hexon protein.

In the present invention, there is also provided a composition comprising the chimeric adenovirus of the present invention. The composition of the present invention is useful for gene therapy or viral therapy, preferably for cancer treatment.

The compositions of the present invention may be formulated so as to provide various formulations together with pharmaceutically acceptable carrier and/or excipient. Thus, the formulations may be in the form of a solution in oil or water medium, suspension or emulsion, extract, powder, granule, tablet or capsule.

For oral formulation, various preparation methods including those specifically designed for adenovirus release may be used, for example, by employing Eudragit or timeclock release system (Lubeck et al., *Proc. Natl. Acad. Sci. USA,* 86(17), 6763-6767 (1989); and Chourasia and Jain, *J. Pharm. Pharm. Sci.,* 6(1), 33-66 (2003)).

As mentioned above, the chimeric adenovirus may be transferred via any gene transfer systems known in the art. A lot of gene transfer system such as those disclosed in [Rolland (1998) *Crit. Rev. Therap. Drug Carrier Systems* 15: 143-198] and the references cited therein are well known in the art. Accordingly, the composition of the present invention may be formulated suitable for these gene transfer system.

The composition of the present invention may comprise any pharmaceutically acceptable carriers known in the art. Examples of suitable carriers are water, salt water, alcohol, lipid, wax, buffer solution, solid carrier such as mannitol, lactose, starches, magnesium stearate, sodium saccharin, talc, cellulose, glucose, sucrose, and magnesium carbonate, or biodegradable microsphere (e.g., polylactate polyglycolate).

The composition of the present invention may be provided in the form of single dose or multi-dose container such as sealed ampule or vial. Preferably, such container may be sealed so as to conserve aseptic condition of pharmaceutical formulations before using. In general, the formulation may be preserved as suspension, fluid, and emlusion in oil or aqueous vehicle. Further, the pharmaceutical formulation may be preserved under freeze drying conditions.

The chimeric adenovirus and the compositions comprising the same may be administered with site-specific injection or intravenous injection. Site-specific injection includes, for example, intraperitoneal injection, intrapleural injection, intrathecal injection, intraarterial injection, intratumoral injection or local application. Such administering methods may be also readily applied to the combination of the treatment utilizing adenoviral vector and the treatment for other target diseases. The preferred method is intravenous injection.

It should be understood that the suitable amount of the active ingredient actually administered ought to be determined in light of various relevant factors including the condition to be treated, the age and weight of the individual patient, food, administration time, excretion rate, the severity of the patient's symptom and reaction susceptibility; and, therefore, the above dose should not be intended to limit the scope of the invention in any way. Generally, the composition of the present invention contains $1\times10^7$ to $1\times10^{13}$ pfu/ml of the present chimeric adenovirus, and the present chimeric adenovirus may be injected in amount of $1\times10^{11}$ pfu once a week for 3 to 5 weeks.

The composition of the present invention may be used as the single therapy. But it may be combined with other anti-tumor protocols, such as conventional chemotherapy or radiation therapy for treating cancer. The chemotherapy drug which can be used with composition of the present invention encompasses paclitaxel, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. The radiation therapy which can be used with the composition of the present invention may be X-ray irradiation and γ-ray irradiation, etc.

The chimeric adenovirus of the present invention hardly renders liver transduction since it does not interact with blood coagulation factors, and exhibits low hepatotoxicity. Accordingly, the high dose of the present chimeric adenovirus may be administered to a subject due to its low risk of immune response and hepatotoxicity and, therefore, the present chimeric adenovirus is useful for safe and efficient gene therapy and viral therapy.

The following examples are intended to illustrate the present invention without limiting its scope.

EXAMPLE 1

Identification of Hexon Gene of SAd19

A hexon gene was amplified from SAd19 using PCR, cloned into a pGEM-T easy vector, and sequenced with an ABI automatic DNA sequencer.

<1-1> Identification of Hexon Gene

The genome of SAd19 was isolated using a DNeasy Tissue Kit (QIAGEN, Germany) and used as a template for the amplification of a hexon gene via PCR with a primer set of SEQ ID NOs: 1 and 2. The amplified hexon gene was purified by Wizard® SV Gel and PCR Clean-Up system (Promega, WI, USA) and inserted into a pGEM-T easy vector (Promega, WI, USA) with the aid of T4 DNA ligase (Roche, Switzerland). The resulting recombinant vector was named pGEM-SAd19 Hexon vector. After transformation of E. coli cells with the vector, the vector DNAs were extracted from 10 clones of the transformants and sequenced by employing an ABI automatic DNA sequencer. Among the 10 base sequences was selected the one which had the highest sequence homology with others, thereby determining the nucleotide sequence of the hexon gene of SAd19 (SEQ ID NO: 3).

<1-2> Comparison with Base and Amino Acid Sequences of Human Adenovirus Serotypes The base and amino acid sequences of the hexon gene of SAd19 were compared with those of 51 human serotype adenoviruses. The hexon of SAd19, belonging to subgroup F, was found to be most similar to that of HAd41, with 85% homology in amino acid sequence therebetween. It showed an amino acid homology of 76% with the hexon of HAd5. Further, the hexon of SAd19 was found to share nucleotide sequence homologies of 76% and 70% with those of HAd41 and HAd5, respectively (FIG. 1).

EXAMPLE 2

Preparation of Chimeric Adenovirus with Hexon of SAd19 Substituted Therein

A shuttle vector for exchanging a hexon gene was constructed and named pHex vector, which is carrying left- and right-extended regions of hexon gene for homologous recombination. The hexon gene of SAd19 was cloned into unique restriction site of pHex vector, locating between left- and right-extended arms of hexon to afford a recombinant vector, named pHex-SAd19 Hexon. SphI-linearized pHex-SAd19 Hexon was subject to homologous recombination with AsiSI-linearized pAd H5_8DS in BJ5183 (Stratagene, CA, USA) to give a SAd19 Hexon-carrying recombinant vector, named pAd H5/S19_8DS. After being linearized with PacI, the pAd H5/S19_8DS was transfected into A549 cells to generate novel chimeric adenovirus with the hexon of SAd19 anchored therein (Ad H5/S19_8DS).

<2-1> Construction of Shuttle Vector

A shuttle vector suitable for the substitution of a hexon gene through homologous recombination was constructed. In this regard, an about 1 kb-long region upstream of the 5' end of the hexon gene of HAd5 was amplified by PCR using a set of the primers of SEQ ID NOs: 4 and 5. The PCR product thus obtained was named Hexon L, and then inserted into pCR2.1 Topo vector (Invitrogen, CA, USA). A DNA sequence analysis allowed the selection of a clone free of mutation, which was named pCR2.1-Hexon L. Separately, an about 1 kb-long region downstream of the 3' end of the hexon gene of HAd5 was amplified by PCR using a set of the primers of SEQ ID NOs: 6 and 7. The PCR product thus obtained was named Hexon R, and then inserted into pCR2.1 Topo vector (Invitrogen, CA, USA). A mutation-free clone, as analyzed by DNA sequencing, was named pCR2.1-Hexon R.

After being excised from pCR2.1-Hexon L by use of both XhoI and EcoRI, Hexon L was inserted into pENTR2B (Invitrogen, CA, USA), which was previously cut with both SalI and EcoRI, to give a recombinant vector, pENTR2B-Hexon L. pCR2.1-Hexon R was digested with HindIII, followed by treatment with a Klenow fragment to make blunt ends. Digestion with EcoRI excised Hexon R from the blunt-ended pCR2.1-Hexon R. This Hexon R was inserted into an Blunted XbaI and EcoRI site of the pENTR2B-Hexon L vector. The resulting recombinant vector was named pHex. PCR was performed in the presence of pfu polymerase (Stratagene, CA, USA) using a set of the primers of SEQ ID NOs: 1 and 2, with pGEM-SAd19 Hexon serving as a template. The Mfe-1-restricted hexon gene of SAd19 was cloned into EcoRI site of pHex vector. The resulting recombinant plasmid, which was found to have the hexon of SAd19 in a correct position as analyzed by DNA sequencing, was named pHex-SAd19 Hexon (FIG. 2A).

<2-2> Substitution with the Hexon of SAd19 Through Homologous Recombination

In order to prepare a chimeric adenovirus recombined with the hexon of SAd19, first, pENTR2B vector (Invitrogen, CA) was treated with EcoRI to remove ccdB region therefrom. The pAAV-CMV_LK8_UN vector, previously constructed by the present inventors (see PCT Publication No. WO2009/102085), was treated with KpnI/BglII to give a CMV_LK8 fragment (later blunt ended) which was then inserted into a KpnI/XhoI site (later blunt ended) of the EcoRI-treated pENTR2B to give a recombinant plasmid pENTR-CMV_LK8.

In order to construct plasmid vector carrying tumor specific expression unit of E1A gene, the proximal promoter region of DNMT-1 (DNA (cytosine-5)-methyltransferase) gene (DS promoter) was amplified from human genomic DNA and cloned into pCR2.1-TOPO vector (Invitrogen, CA) to give a recombinant plasmid pCR-DS. Gene amplification was conducted in the presence of Ex-Taq polymerase (Takara, Japan) by PCR using human genomic DNA as PCR template and a set of the primers of SEQ ID NO: 8 (5'-CTT CTC GCT GCT TTA TCC CCA TC-3') and SEQ ID NO: 9 (5'-CTC GGA GGC TTC AGC AGA CGC-3'), which binds to both ends of proximal promoter region of DNMT-1 gene. Starting from denaturation at 94° C. for 5 min, PCR was performed with 30 cycles of denaturing at 94° C. for 30 sec, annealing at 56° C. for 30 sec and extension at 72° C. for 1 min, followed by extension at 72° C. for additional 3 min.

A DNA fragment excised from pCR-DS by SacI and XhoI was inserted ClaI and SalI sites in front of mutant E1A gene in the pΔE1Sp1B-E2F-1 Rb7Δ19k vector (Kim, J., et al. (2007) *Hum. Gene Ther* 18, p 773-786; mE1A, Korean Patent No. 746122; ΔE1B19K, Korean Patent No. 432953) to construct a recombinant plasmid pSP72-DS_mE1A_ΔE1B19K. A fragment resulting from the treatment of pSP72-DS_mE1A_ΔE1B19K with BamHI was inserted into a BglII site of pENTR-CMV_LK8 to afford a shuttle vector, named pENTR-CMV_LK8-DS_mE1A_ΔE1B19K.

To a mixture of 100 ng of pAd-PL Dest (Invitrogen, CA, USA) and 500 ng of pENTR-CMV_LK8-DS_mE1A_ΔE1B19K was added 16 μL of clonase I reaction buffer (Invitrogen, CA, USA). The reaction mixture was incubated at room temperature for 1 hr with 2 μL of clonase I and then at 37° C. for 10 min with 2 μL of proteinase K (2 μg/μL). 10 μL of the resulting reaction mixture was taken and used to transform *E. coli* DH5α competent cells which were then spread over ampicillin plates. Plasmid DNA extracted from colony positive in the restriction mapping was identified by DNA sequencing analysis as an adenovirus vector of interest, and then named pAd H5-8DS.

Figure 2B:
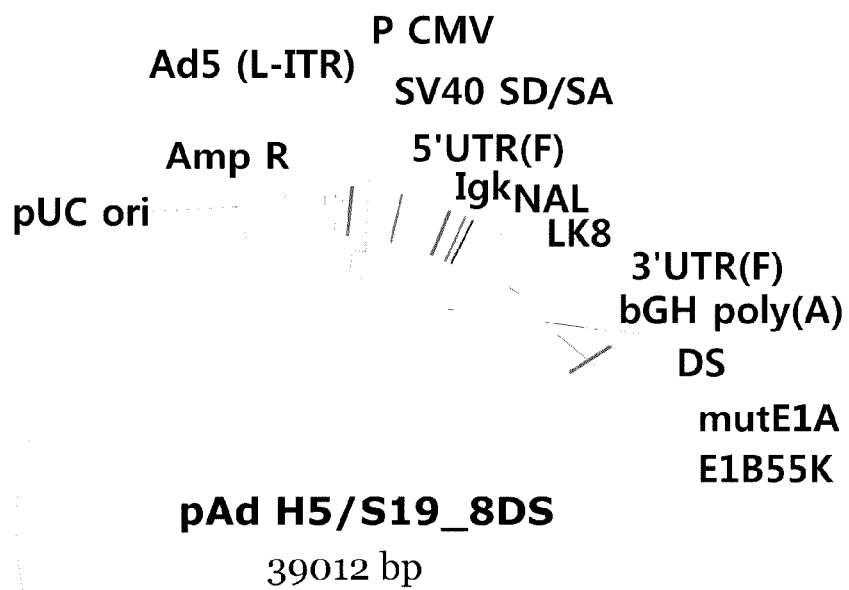
FIG. 2B: cleavage maps of pAd H5/S19_8DS vector.

In order to substitute the hexon gene of pAd H5_8DS with SAd19 Hexon, first, 500 ng of pHex-SAd19 Hexon and 50 ng of pAd H5_8DS were linearized respectively with SphI and AsiSI and mixed together before transformation into *E. coli* BJ5183 by electroporation. Homologous recombination was screened by PCR using a set of the primers of SEQ ID NO: 10 (5'-ATG CGC AAG GTG TAG CCA-3') and SEQ ID NO: 11 (5'-AGC GTG CTG GCC AGC GTG-3'), which were designed to examine homologous recombination. Starting from denaturation at 94° C. for 5 min, PCR was performed with 30 cycles of denaturation at 94° C. for 30 sec, annealing at 55° C. for 40 sec and extension at 72° C. for 1.5 min, followed by extension at 72° C. for an additional 3 min. The positively screened colonies were subjected to secondary screening by PCR using a set of the primers of SEQ ID NO: 12 (5'-CCC GTT ACA TAA CTT ACG-3') (CMV sense primer) and SEQ ID NO: 13 (5'-TTA TGG CCT GGG GCG TTT ACA G-3') (E1A antisense primer), which were designed to amplify a region comprising both LK8 and E1A genes. Starting from denaturation at 94° C. for 5 min, the PCR was performed with 30 cycles of denaturation at 94° C. for 30 sec, annealing at 55° C. for 40 sec and extension at 72° C. for 30 sec, followed by extension at 72° C. for an additional 5 min. DNA was isolated from the clones which were positively screened by the two PCRs and was amplified in *E. coli* DH5α. A clone which was coincident in all the cutting patterns with EcoRI, SpeI, XbaI and PshAI was secured and named pAd H5/S19_8DS (FIG. 2B). DNA sequencing again identified that pAd H5/S19_8DS contained the hexon of SAd19.

Figure 2C:
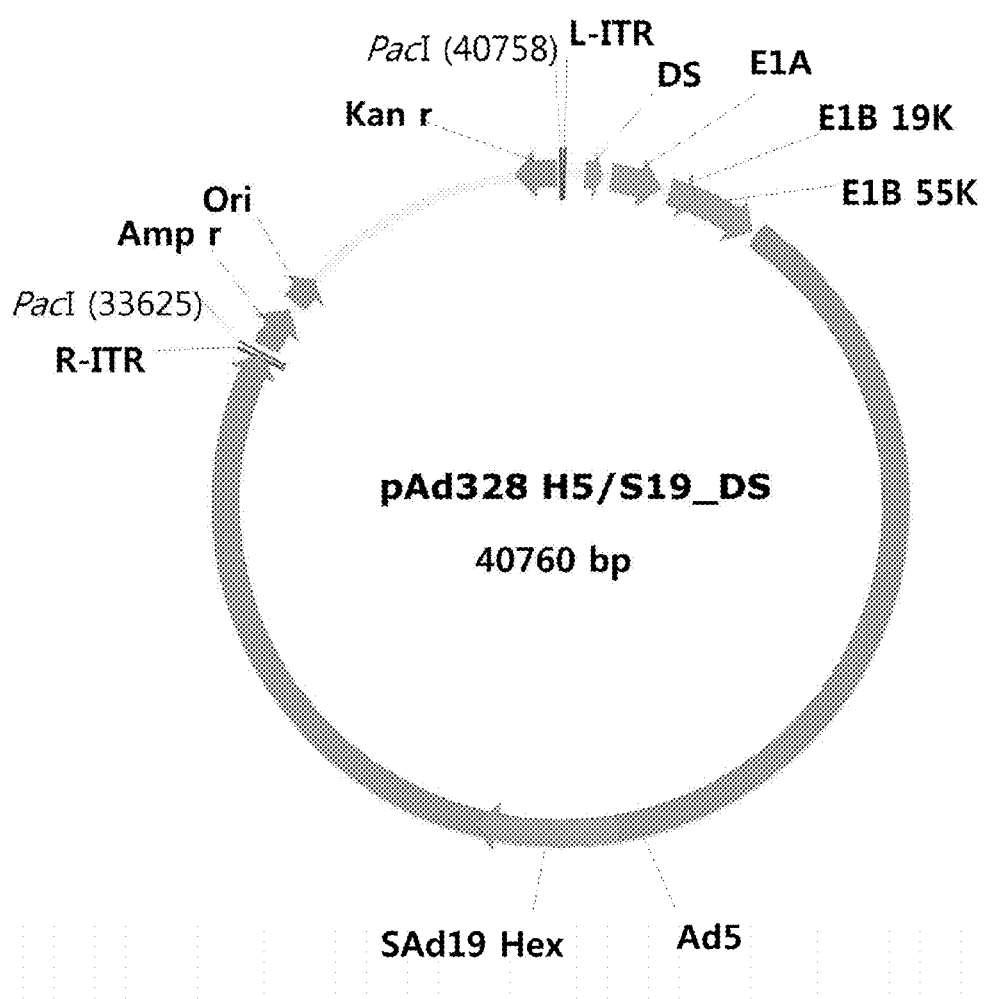
FIG. 2C: cleavage maps of pAd328 H5/S19_DS vector.
Figure 2D:
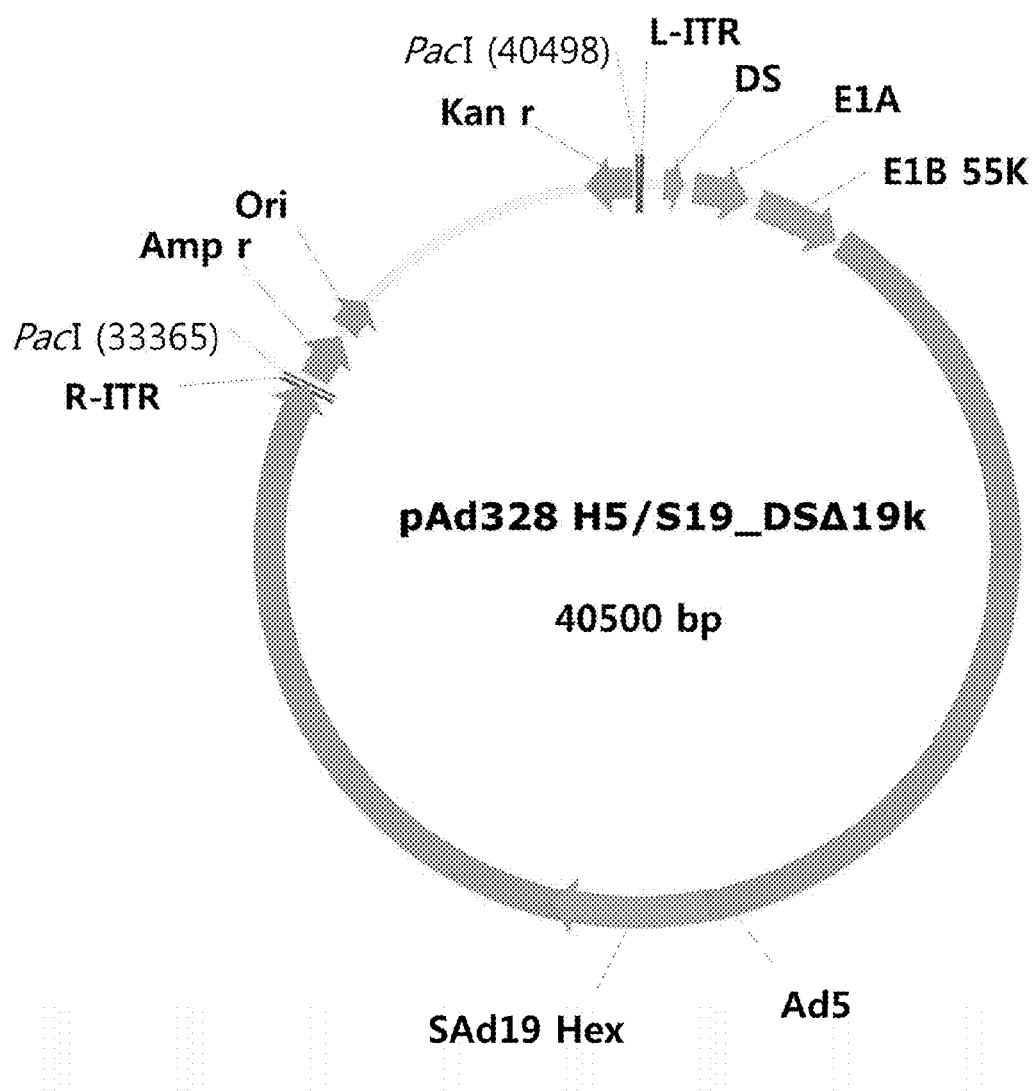
FIG. 2D: cleavage maps of pAd328 H5/S19_DS Δ19k.

A DNA fragment containing DS promoter was excised from pCR-DS by EcoRI digestion and cloned into the EcoRI site of phRL-null vector (Promega, WI, USA) to generate phRL-DS. A fragment resulting from the treatment of phRL-DS with SalI and PstI was inserted into the SalI and PstI sites of pE1.2 (O.D.260 Inc. Boise, Id. US) shuttle vector, generating pE1.2-DS. The DNA fragment of 1.7 kb size excised from pE1.2-DS by AlwNI digestion was cloned to SfiI site of pAd328 (O.D.260 Inc. Boise, Id. US) by enzyme-ligation method using *E. coli* XL1-blue electro-competent cells. Plasmid DNA extracted from colony growing on LB plate supplemented with ampicillin and kanamycin was secured by coincidence in all the cutting patterns with EcoRI, SpeI, XbaI and PshAI and named pAd328-DS adenoviral vector (FIG. 2C). The adenovirus E1 gene was amplified from genomic DNA of HAd5 and cloned to pGEM-T easy vector (Promega, WI, USA) to give a recombinant plasmid pGEMT-Ad E1. The pGEMT-Ad E1 was treated very shortly with EcoNI after BssHI digestion to remove a E1B19k region therefrom. E1B19k-deleted pGEMT-Ad E1 was named to pGEMT-Ad E1 Δ19k. In order to substitute the E1 gene of pAd328-DS with E1BΔ19k-deleted E1 gene, first, 100 ng of pAd328-DS and 1 μg of SphI-linearized pGEMT-Ad E1 Δ19k were mixed together before transformation into *E. coli* BJ5183 by electroporation. Homologous recombination was screened by digestion with HindIII, SphI and EcoRV. A clone which was coincident in all the cutting patterns was secured and named pAd328-DSΔ19k. According to above procedure described to make pAd H5/S19 8DS plasmid, pAd328 H5/S19_DS and pAd328 H5/S19_DSΔ19k were generated by homologous recombination between pHex-SAd19 Hexon and pAd328_DS or pAd328-DSΔ19k (FIG. 2D).

<2-3> Preparation of Chimeric Adenovirus Recombined with the Hexon of SAd19

The plasmid pAd H5/S19_8DS was linearized with PacI and transfected into A549 cells. 14 Days after the transfection, the cells were observed to undergo cytopathy, and thus collected along with the medium. In order to completely separate the virus therefrom, first, the cells were frozen and thawed three times, followed by centrifugation. The supernatant containing the virus was subjected to two rounds of plaque purification to give pure virus, named Ad H5/S19_8DS virus. Ad H5/S19_8DS virus was identified as chimeric adenovirus having the hexon gene of SAd19 as analyzed by sequencing of their genomic DNA. Ad328 H5/S19_DS and Ad328 H5/S19_DSΔ19k virus were prepared as the above-mentioned procedure for the generation of Ad H5/S19_8DS.

13

<2-4> Production and Purification of Chimeric Adenovirus Having Hexon of SAd19

A549 lung cancer cells were grown at 80% confluency in 30 culture dishes of 150 mm-size and then infected with Ad H5/S19_8DS virus at MOI of 20. After incubation at 37° C. for two days, the cells were harvested by centrifugation at 12,000×g for 10 min and then suspended in 10 mL of lysis buffer (0.5M Tris, pH8.0, 1 mM $MgCl_2$). Three rounds of freezing and thawing lysed the cells, followed by refrigerated centrifugation at 12,000×g for 10 min to remove cell debris. In order to prepare a discontinuous CsCl gradient, 8 mL of a CsCl solution having a specific gravity of 1.4 was placed into an ultracentrifuge tube (Beckman, CA, USA) and covered with 6 mL of a CsCl solution having a specific gravity of 1.2 in such a manner as to keep the boundary therebetween definitely. A virus sample filtered through a 0.22 μm filter was loaded onto the CsCl 1.4/1.2 gradient so as not to dishevel the boundary, and the tube was weight balanced with 10 mM Tris-HCl (pH7.9). The tube was applied to a SW28 rotor and ultra-centrifuged at 23,000 rpm for 90 min under a refrigerated condition to form a virus band.

The virus thus separated was again purified using a continuous CsCl gradient ultracentrifugation process. For this, 8 mL of a CsCl solution having a specific gravity of 1.4 was placed in an ultracentrifuge tube (Beckman, CA, USA) and then covered with 6 mL of a CsCl solution having a specific gravity of 1.2 in such a manner as to keep a definite boundary therebetween. Using a gradient station (Biocomp, Canada), a continuous gradient was formed in the tube. The virus sample obtained by the discontinuous CsCl gradient ultracentrifugation was diluted with one volume of 10 mM Tris-HCl (pH7.9) and loaded into the CsCl 1.4/1.2 gradient tube so as not to blur the boundary therebetween. After being weight balanced with 10 mM Tris-HCl (pH7.9), the tube was ultra-centrifuged at 23,000 rpm for 90 min under a refrigerated condition to form a virus band. It was dialyzed three times with PBSG buffer (PBS containing 10% Glycerol), while exchanging the buffer with fresh one every 6 hrs.

EXAMPLE 3

In vitro Study of Chimeric Adenovirus Having the Hexon of SAd19

Ad H5/S19_8DS virus was in vitro assayed for selectivity for lung cancer by comparing expression levels of E1A and LK8 in the lung cancer cell line A549 and the normal cell line MRCS both of which were infected at various MOIs with the virus. In addition, Ad H5/S19_8DS virus was measured for affinity for the coagulation factors which mediate blood-circulating virus to liver.

<3-1> MOI-Dependent E1A Expression

Figure 3:
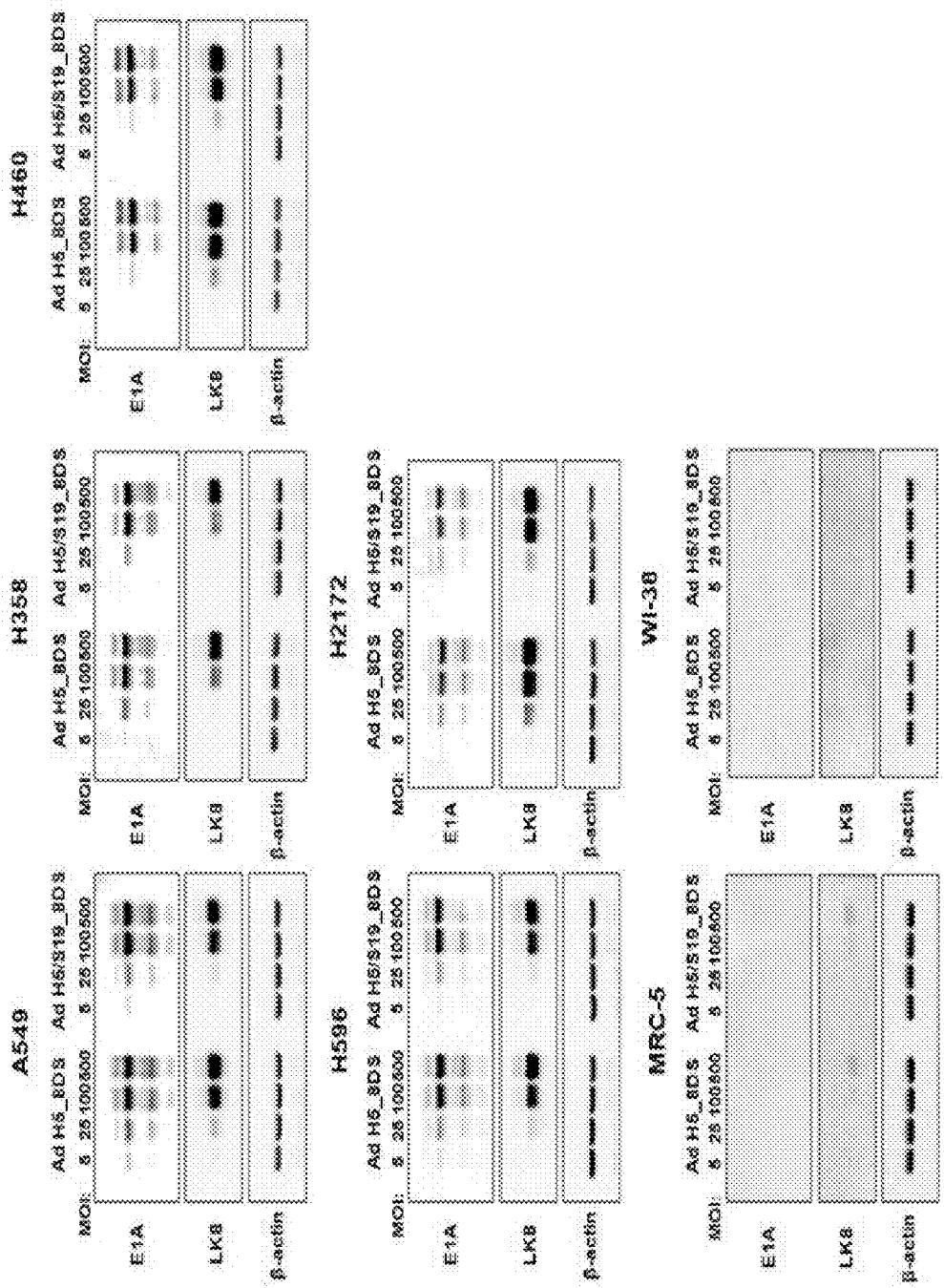
FIG. 3: the results of western blot analysis showing the expression level of tumor-specific E1A proportional to infected units of Ad H5_8DS and Ad H5/S19_8DS.

A549 lung cancer cells and MRCS normal cells, which were both grown at about 80% confluency in 6-well plates, were infected with Ad H5/S19_8DS virus at an MOI of 100, 25, 10 and 1. After incubation at 37° C. for 24 hrs, the cells were harvested by centrifugation at 3,000 rpm for 5 min, suspended in 1×SDS-PAGE buffer (50 mM Tris(pH6.8), 2% SDS, 100 mM dithiothreitol, 0.1% bromophenol blue, 10% Glycerol), heated at 100° C. for 5 min in a water bath, and centrifuged at 10,000 rpm for 2 min. The resulting supernatant was electrophoresed at 20 mA for about 2 hrs on 4-12% SDS-PAGE gel (Invitrogen, CA, USA). The protein bands separated on the gel were transferred for about 90 min onto a PVDF membrane using a transfer unit (Invitrogen, CA, USA) in Tris-Glycine buffer (39 mM Glycine, 48 mM Tris, 0.037% SDS, 20% methanol) with an electric field of 300 mA applied thereto. The membrane was blocked at room temperature for one hour with a TBS Blocking solution (Thermo Scientific, IL, USA). A mouse anti-E1A monoclonal antibody(BD Pharmingen, CA, USA), serving as a primary antibody, was 1:3,000 diluted with 5% skim milk/1×TBST buffer, probed at room temperature for one hour and washed for six times each for 5 min with 1×TBST buffer. Anti-mouse HRP(KPL, MA, USA), serving as a secondary antibody, was 1:5,000 diluted with 5% skim milk/1×TBST buffer, probed for 30 min, washed six times each for 5 min with 1×TBST buffer, and reacted with a color developing agent (ECL, Amersham, UK) to visualize an E1A protein band. The expression level of E1A was increased in a MOI-dependent manner, being 100-fold higher in A549 cancer cells than in MRC-5 normal cells (FIG. 3).

<3-2> Affinity for Coagulation Factor X

Figure 4A:
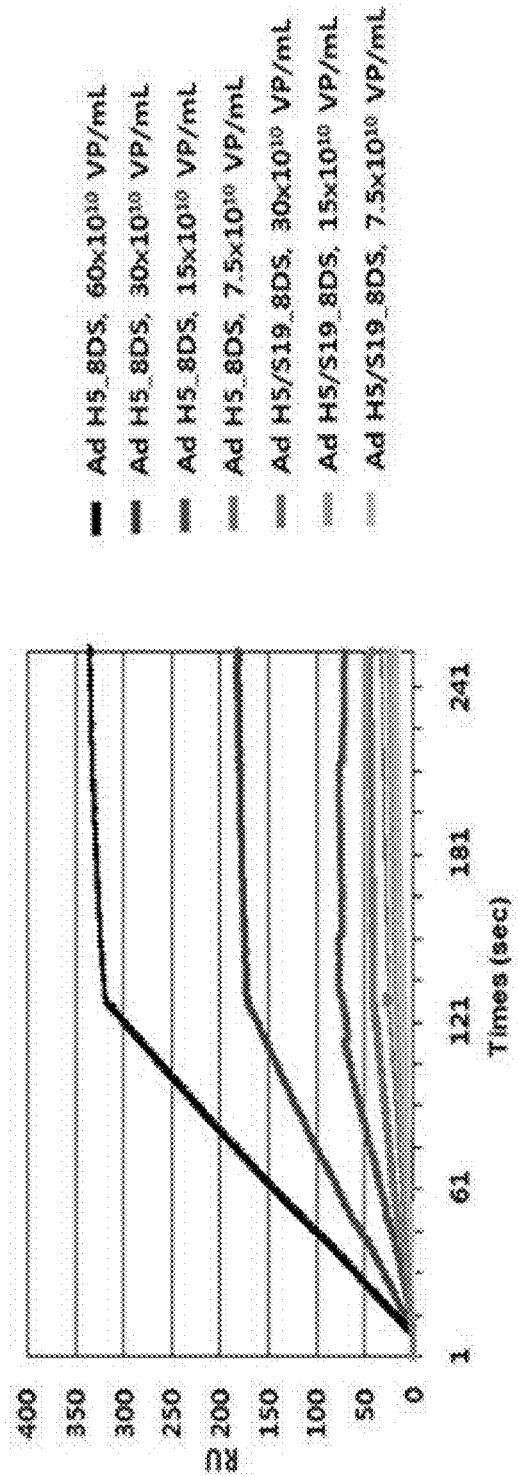
FIG. 4A: SPR results for measuring the binding affinity between human blood coagulating factor X and Ad H5/S19_8DS (A)
Figure 4B:
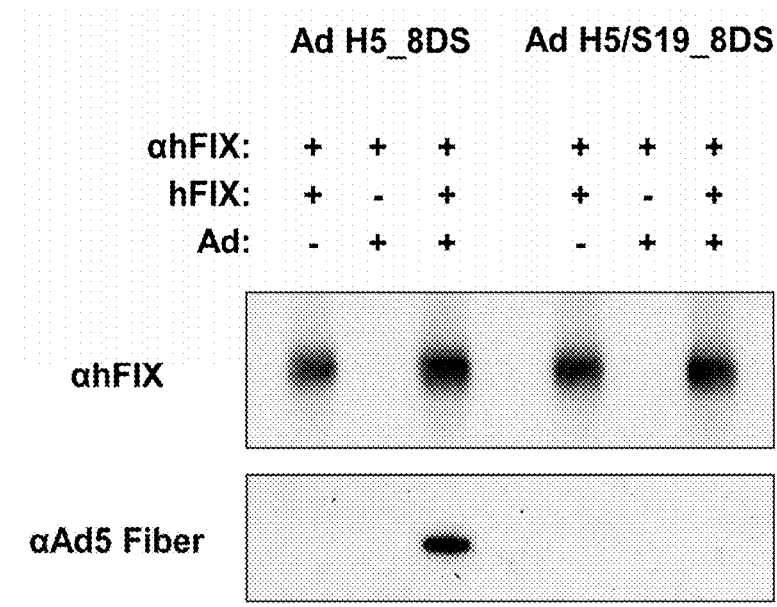
FIGS. 4B-4D: western blot result for human blood coagulating factor and adenoviral fiber protein after co-immunoprecipitation of human blood coagulating factor IX or X with either Ad H5_8DS, Ad H5/S19_8DS, Ad328 H5/S19_DS or Ad328 H5/S19_DS Δ19k.
Figure 4C:
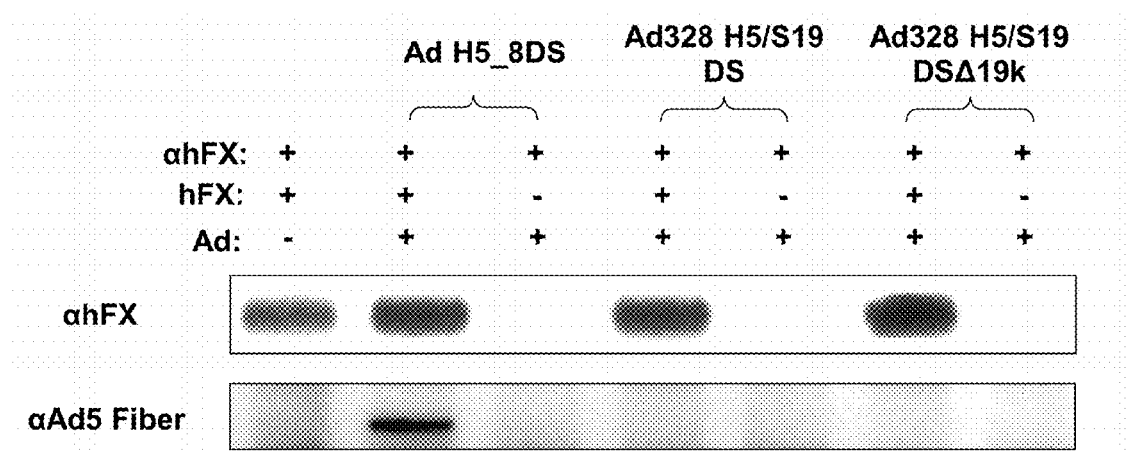
Figure 4D:
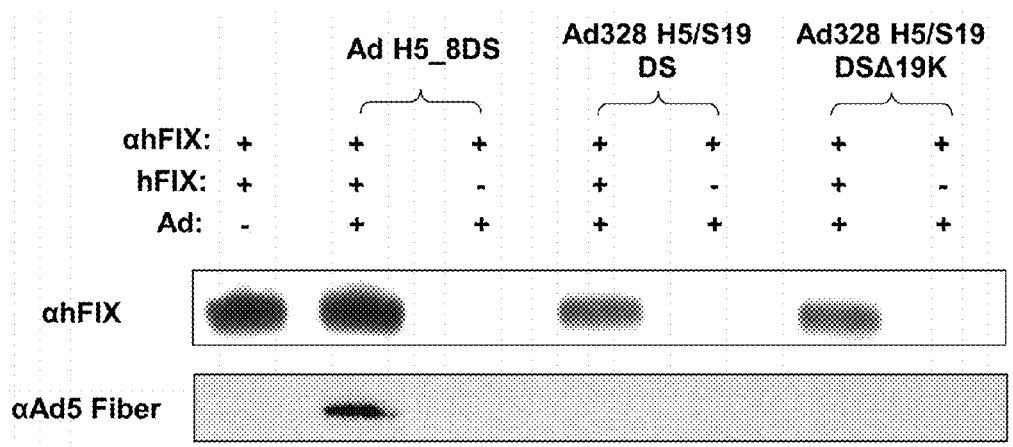

Ad H5/S19_8DS was analyzed for affinity for coagulation factor X using an SPR (Surface Plasmon Resonance) method. Purified coagulation factor X (HCX-0050, Haematological Technologies Inc., VT, USA) was applied to a CS5 sensor chip (Biacore, Sweden). Each of the purified Ad H5_8DS and Ad H5/S19_8DS viruses was diluted at concentrations of $3.0 \times 10^{11}$ VP/mL, $1.5 \times 10^{11}$ VP/mL and $0.75 \times 10^{11}$ VP/mL in HBSP buffer (10 mM HEPES pH7.4, 150 mM NaCl, 0.005% Tween 20) containing 5 mM $CaCl_2$. HBSEP (10 mM HEPES pH 7.4, 150 mM NaCl, 3 mM EDTA, 0.005% Tween 20) was used as regeneration buffer for detaching virus from the chip. While the virus solution was passed over the coagulation factor X-immobilized CMS sensor chip at a flow rate of 30 μL/min, RU values were recorded. At the three different concentrations, the adenovirus serotype 5 Ad H5_8DS showed SPR signals for immobilized factors of 300, 150 and 70RU, respectively, whereas Ad H5/S19_8DS, the chimeric adenovirus having the hexon of SAd19, showed very weak or little affinity for coagulation factor X as the SPR signals were found to be within 5RU at all the three concentrations (FIG. 4A). Ad328 H5/S19_DS and Ad328 H5/S19_DS Δ19k were also assayed for affinity for coagulation factor X by an immunoprecipitation method as described in <3-3> below using coagulation factor X protein instead of factor IX (FIG. 4D).

<3-3> Affinity for Coagulation Factor IX

Ad H5/S19_8DS was assayed for affinity for coagulation factor IX using an immunoprecipitation method. To 1 mL of PBS in a tube was added $1 \times 10^{11}$ VP of Ad H5_8DS or Ad H5/S19_8DS, together with 10 μg of purified coagulation factor IX (HCIX-0040, Haematological Technologies Inc., VT, USA), 5 μg of a goat anti-coagulation factor IX antibody and 50 μL of sepharose-protein G (50% slurry), followed by incubation at 4° C. for 2 hrs in an orbital shaker. After centrifugation at 5,000 rpm for 5 min, the sepharose-protein G pellet thus obtained was washed three times with PBS, suspended in 100 μL of 1×SDS-PAGE sample buffer (50 mM Tris(pH6.8), 2% SDS, 100 mM dithiothreitol, 0.1% bromophenol blue, 10% Glycerol), and heated for 5 min. The suspension was centrifuged and the resulting supernatant was electrophoresed at 20 mA for about 2 hrs on 4~12% SDS-PAGE gel. The proteins thus separated were transferred for about 90 min onto a PVDF membrane in a transfer unit containing Tris-Glycine buffer (39 mM Glycine, 48 mM Tris, 0.037% SDS, 20% methanol) to which 300 mA was applied. The membrane was blocked at room temperature for one hour with a TBS Blocking solution (Thermo Scientific, IL, USA). A mouse anti-HAd5 fiber monoclonal antibody (NeoMarkers, CA, USA), serving as a primary antibody, was 1:3,000 diluted with 5% skim milk/1×TBST buffer, probed at room temperature for one hour and washed six times with each for 5 min 1×TBST buffer. Anti-mouse HRP(KPL, MA, USA), serving as a secondary antibody, was 1:5,000 diluted with 5% skim milk/1×TBST buffer, probed for 30 min, washed six times each for 5 min with 1×TBST buffer, and reacted with a color developing agent (ECL, Amersham, UK) to visualize a fiber band. The blots on the PVDF membrane were immersed for one hour in Restore™ Western Blot Stripping Buffer (Thermo Scientific, IL, USA) with shaking in an orbital shaker, washed three times each for 10 min with 1×TBST buffer, and blocked at room temperature for one hour with a TBS Blocking solution. A sheep anti-coagulation factor IX antibody (Affinity Biologicals, Canada), used as a primary antibody, was 1:3,000 diluted with 5% skim milk/1×TBST buffer, probed at room temperature for one hour, and washed six times each for 5 min with 1×TBST buffer. Anti-sheep HRP (KPL, MA, USA), serving as a secondary antibody, was 1:5,000 diluted with 5% skim milk/1×TBST buffer, probed for 30 min, washed for 5 min six times with 1×TBST buffer, and reacted with a color developing agent (ECL, Amersham, UK) to visualize a coagulation factor IX band (FIG. 4B). Ad328 H5/S19_DS and Ad328 H5/S19_DS Δ19k were also assayed for affinity for coagulation factor IX using an immunoprecipitation method as described above (FIG. 4C).

EXAMPLE 4

In vivo Study of Chimeric Adenovirus Having the Hexon of SAd19

<4-1> Biodistribution

Figure 5A:
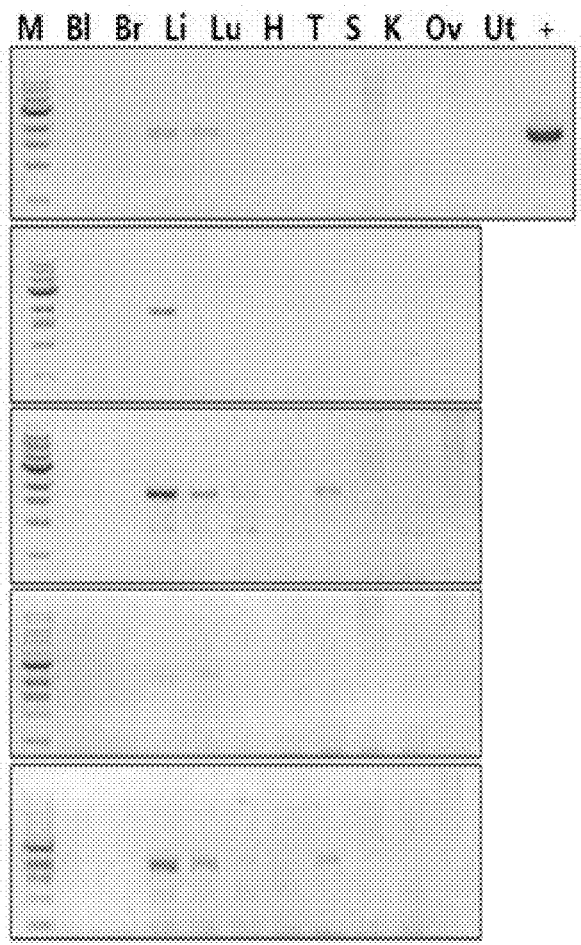
FIGS. 5(A) and 5(B): results of agarose gel electrophoresis showing the PCR-amplified DNA bands of adenoviral fiber gene in respective organs after intravenous injection of Ad H5_8DS (FIG. 5(A)) and Ad H5/S19_8DS (FIG. 5(B))
Figure 5B:
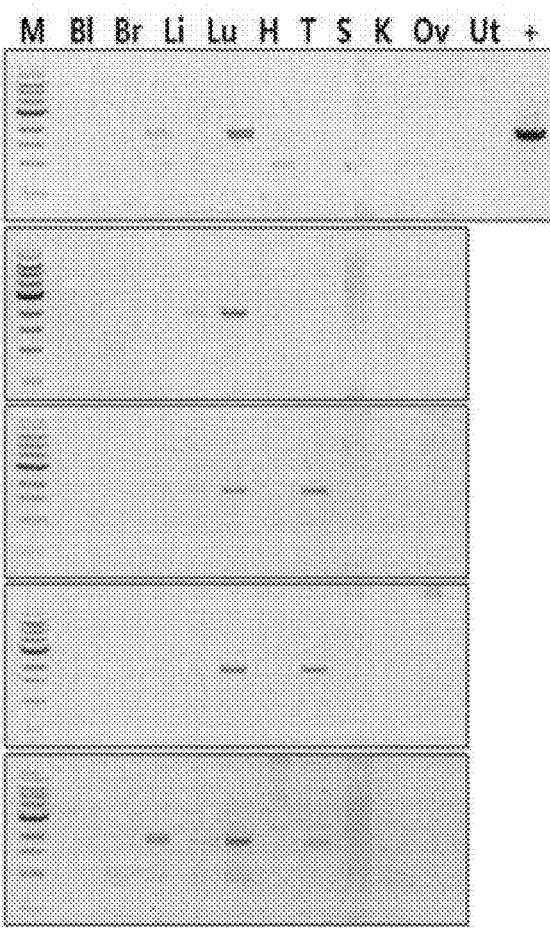

Ad H5/S19_8DS was intravenously injected in a dose of $3 \times 10^{10}$ VP into Balb/c normal mice and nude mice, both 6 weeks old. Two days after injection, DNA was isolated from the brain, the liver, the lung, the heart, the thymus, the spleen, the ovary, the uterus and blood using a DNeasy Blood and Tissue Kit (QIAGEN, Germany). The isolated DNA was quantitatively analyzed using an OD spectrophotometer and used in an amount of 200 ng as a template for PCR. The E4 region of adenovirus was amplified by PCR using a set of primers of SEQ ID NO: 14 (5'-ACT CGA GCA CGT TGT GCA TTG TCA-3') and SEQ ID NO: 15 (5'-TGT CGA CTA GTT TTC TTA AAA TGG-3'). Starting from denaturation at 94° C. for 5 min, PCR was performed with 30 cycles of denaturation at 94° C. for 30 sec, annealing at 55° C. for 40 sec and extension at 72° C. for 1 min, followed by extension at 72° C. for additional 3 min. The PCR products were run on 1% agarose gel in the presence of an electric field to analyze the distributions of adenovirus by organs. When injected, the HAd5, i.e., Ad H5_8DS, was most highly observed in the liver and the lung, and partially detected in the heart and the spleen. In contrast, the chimeric adenovirus having the hexon of SAd19, Ad H5/S19_8DS virus, was mostly detected in the heart and the spleen, and only a part was detected in the liver and the lung (FIGS. 5(A) and 5(B)). This distribution pattern is quite different from the biodistribution of adenovirus serotype 5, which is known to be transduced into the liver upon intravenous injection and induce hepatotoxicity upon injection in large doses. That is, Ad H5/S19_8DS virus was transduced in a very small amount into the liver, as inferred from the observation of Example <3-2> that the virus showed little affinity for coagulation factor X.

EXAMPLE 5

Figure 6A:
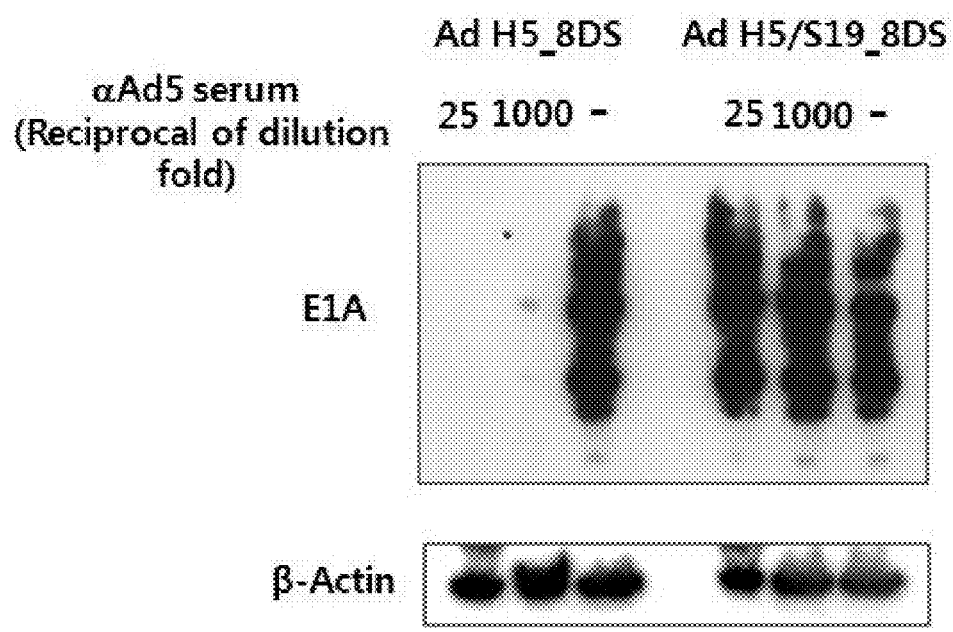
FIGS. 6A-6B: Western blot analysis results demonstrating the infection-evading ability of chimeric adenoviruses having hexon of simian adenovirus serotype 19, Ad H5/S19_8DS (A), Ad328 H5/S19_DS and Ad328 H5/S19_DS Δ 19k (B), by employing neutralizing antibodies against HAd5.
Figure 6B:
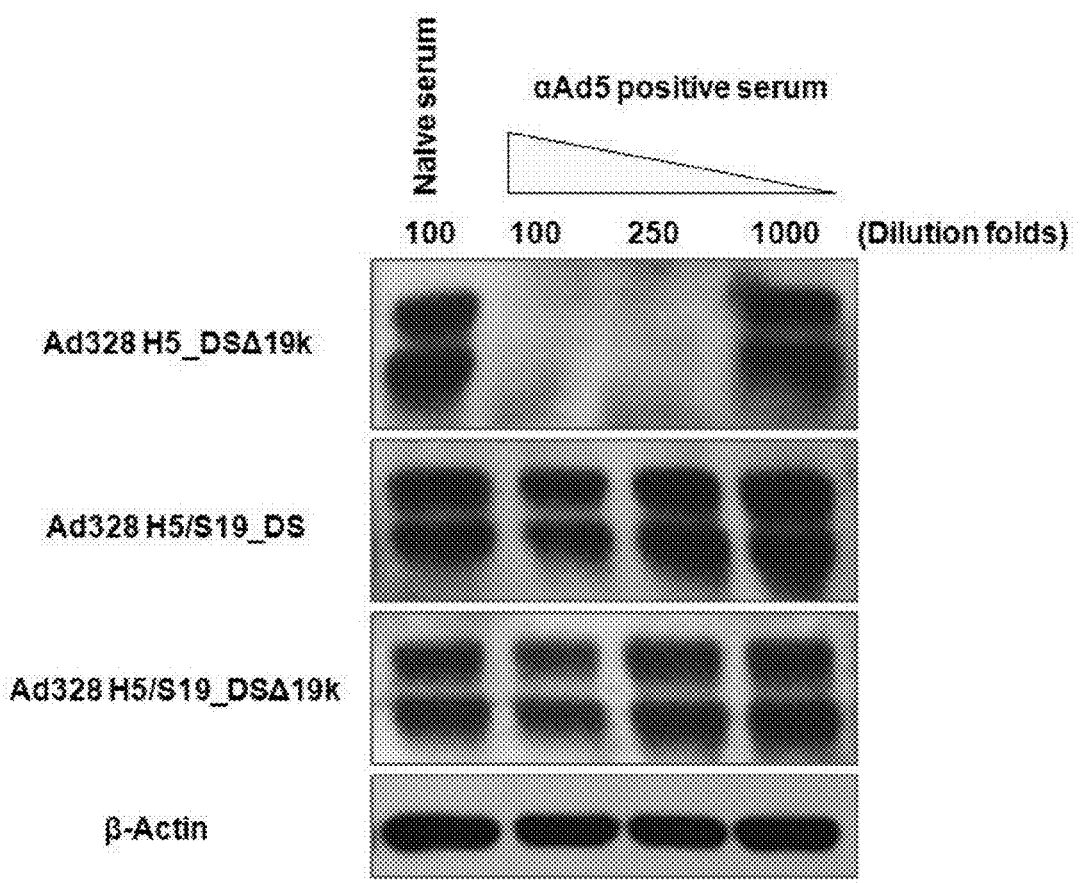

In vitro Assay for Ability of Chimeric Adenovirus Having the Hexon of SAd19 to Evade Immune Recognition of HAd5 Neutralizing Antibody <5-1> Examination of the Effect of Anti-HAd5-Positive Plasma on Transduction of Ad H5/S19_8DS and Ad328 H5/S19_DS by E1A Expression Pattern Wild-type HAd5 was intramuscularly injected at a dose of $1 \times 10^{11}$ VP into the hind legs of mice and two weeks thereafter, the same dose of the virus was injected again to boost an immune response. Sera were separated from the blood taken from all of the virus-injected mice and then measured for anti-adenovirus antibody levels. In this regard, 1/25, 1/100, and 1/1,000 dilutions of the sera were added to adenovirus-coated ELISA plates, incubated for one hour, and washed three times with PBST (PBS containing 0.1% Tween20), followed by incubation for one hour with a 1/5,000 dilution of an HRP-conjugated anti-mouse IgG antibody. After the plates were washed five times with PBST (PBS containing 0.1% Tween20), a color was developed by reaction for 30 min with a TMB substrate and termination with 1 M phosphoric acid. The plates were measured for absorbance. They were regarded as inducing a positive immune response when the absorbance thereof was 50% or higher as compared with that of a positive control, prepared by reacting with a 1/1000 dilution of an anti-adenovirus antibody (AbD Serotec, NC, USA). A549 cells, grown at 90% confluency in 6-well plates, were infected at MOI of 25 with Ad H5/S19_8DS or Ad328 H5/S19_DS one hr before being incubated at room temperature with the mouse plasma which were determined to be of positive immune response. After incubation at 37° C. for 24 hrs, the cells were harvested by centrifugation at 3,000 rpm for 5 min, suspended in 1×SDS-PAGE sample buffer (50 mM Tris (pH6.8), 2% SDS, 100 mM dithiothreitol, 0.1% bromophenol blue, 10% glycerol), heated at 100° C. for 5 min in a water bath, and centrifuged at 10,000 rpm for 2 min. The clarified supernatant was run for about 2 hrs on 4-12% SDS-PAGE gel in the presence of 20 mA using an electrophoresis kit (Novex). The separated proteins were transferred for 90 min onto a PVDF membrane in a transfer unit (Novex) containing Tris-Glycine buffer (39 mM Glycine, 48 mM Tris, 0.037% SDS, 20% methanol) with an electric field of 300 mA applied thereinto. The membrane was blocked at room temperature for one hour with a TBS Blocking solution (Thermo Scientific, IL, USA). The membrane was incubated at room temperature for one hour with a 1:3,000 dilution of mouse anti-E1A monoclonal antibody (BD Pharmingen, CA, USA), a primary antibody, in 5% skim milk/1×TBST buffer and then washed six times each for 5 min with 1×TBST buffer. Incubation with a 1:5,000 dilution of anti-mouse HRP (KPL, MA, USA) as a secondary antibody in 5% skim milk/1× TBST buffer for 30 min was followed by washing six times each for 5 min with 1×TBST buffer. An E1A protein band was visualized with a color developing reagent (ECL, Amersham, UK). Whereas the transduction of Ad H5_8DS was inhibited by the anti-HAd5 antibody-positive plasma, there were no effects of the anti-HAd5 antibody-positive plasma on the transduction of the chimeric adenovirus Ad H5/S19_8DS (FIG. 6A), Ad328 H5/S19_DS and Ad328 H5/S19_DS Δ 19k (FIG. 6B).

<5-2> Examination of the Effect of Anti-HAd5-Positive Plasma on H5/S19_8DS Transduction by Immunostaining After being incubated at room temperature for one hour with the mouse plasmas which were determined to be of positive immune response, 90% confluently cultured A549 cells were infected with Ad H5/S19_8DS or Ad H5/S19_DS at an MOI of 25, followed by incubation at 37° C. for two days. The cells were fixed with cold methanol and blocked for one hour with a protein-free T20 (TBS) blocking buffer (Thermo Scientific, IL, USA). The cells were incubated for one hour with a dilution (1/3,000) of a mouse anti-E1A monoclonal antibody (BD Pharmingen, CA, USA) in PBST buffer and washed six times each for 5 min with PBST buffer. Then, the cells were again treated for one hour with a dilution (1/5,000) of a HRP-conjugated anti-mouse secondary antibody in PBST buffer, washed six times each for 5 min with PBST buffer, and reacted with a DAB solution to produce a color. The anti-HAd5 antibody-positive plasma was found to inhibit the transduction of Ad H5_8DS, but to have no influence on the transduction of the chimeric adenovirus Ad H5/S19_8DS (FIGS. 7A and 7B), Ad328 H5/S19_DS and Ad H5/S19_DSΔ19k (FIG. 7C).

<5-3> In vivo Examination into Ability of Chimeric Adenovirus Having the Hexon of SAd19 to Evade Immune Recognition of HAd5 Neutralizing Antibody Wild-type HAd5 was intramuscularly injected at a dose of $1\times10^{11}$ VP into the hind legs of hamster and, two weeks thereafter, which the same dose of the virus was injected again to induce an immune response. Sera were separated from the blood taken from all of the virus-injected hamsters and then measured for anti-adenovirus antibody level therein. In this regard, 1/25, 1/100, and 1/1,000 dilutions of the sera were added to adenovirus-coated ELISA plates, incubated for one hour, and washed three times with PBST (PBS containing 0.1% Tween20), followed by incubation for one hour with a 1/5,000 dilution of an HRP-conjugated anti-hamster IgG antibody. After the plates were washed five times with PBST (PBS containing 0.1% Tween20), a color was developed by reaction for 30 min with a TMB substrate and termination with 1 M phosphoric acid. The plates were measured for absorbance. They were regarded as inducing a positive immune response when the absorbance thereof was 50% or higher as compared with that of a positive control, prepared by reacting with a 1/1,000 dilution of an anti-adenovirus antibody. The immunized hamsters into which HAd5, i.e., Ad H5_8DS was intravenously injected at a dose of $1\times10^{11}$ VP was found to be too low in blood LK8 level to detect. In contrast, the intravenous injection of Ad H5/S19_8DS at a dose of $1\times10^{11}$ VP ensured a blood LK8 level of 200 ng/mL or higher, and the expression amount was maintained at a level of 200 ng/mL or higher for 28 days, indicating that the chimeric adenovirus having the hexon of SAd19 is not inhibited on their transduction by the anti-human adenovirus serotype 5 neutralizing antibody (FIG. 8).

EXAMPLE 6

Toxicity of Chimeric Adenovirus Having the Hexon of SAd19

Figure 9A:
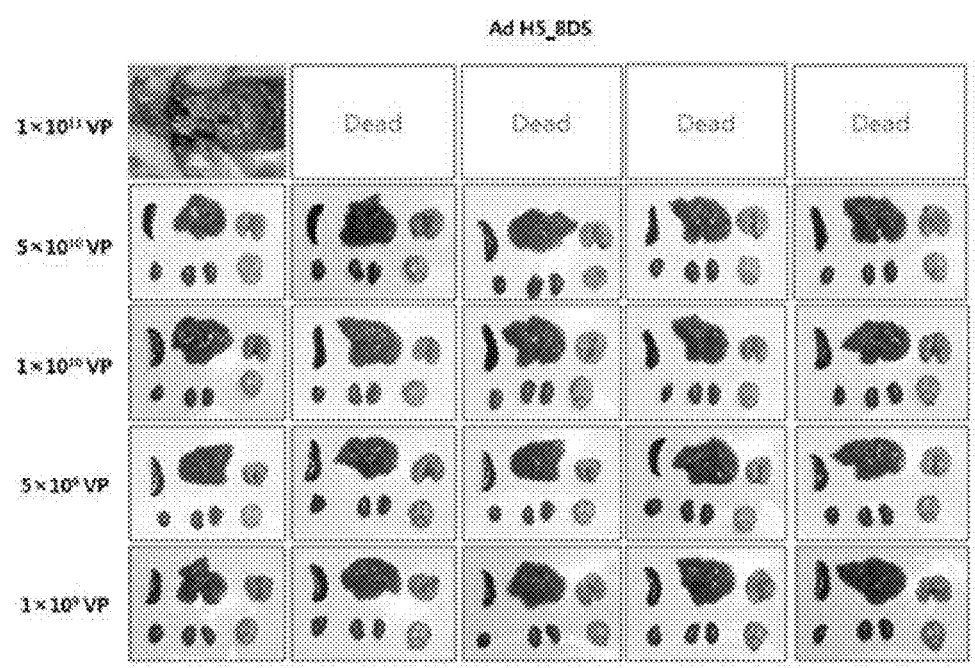
FIGS. 9(A) and 9(B): a photograph of each organ excised from autopsied mice into which Ad H5_8DS and Ad H5/S19_8DS are intravenously administered dose-dependently.
Figure 9B:
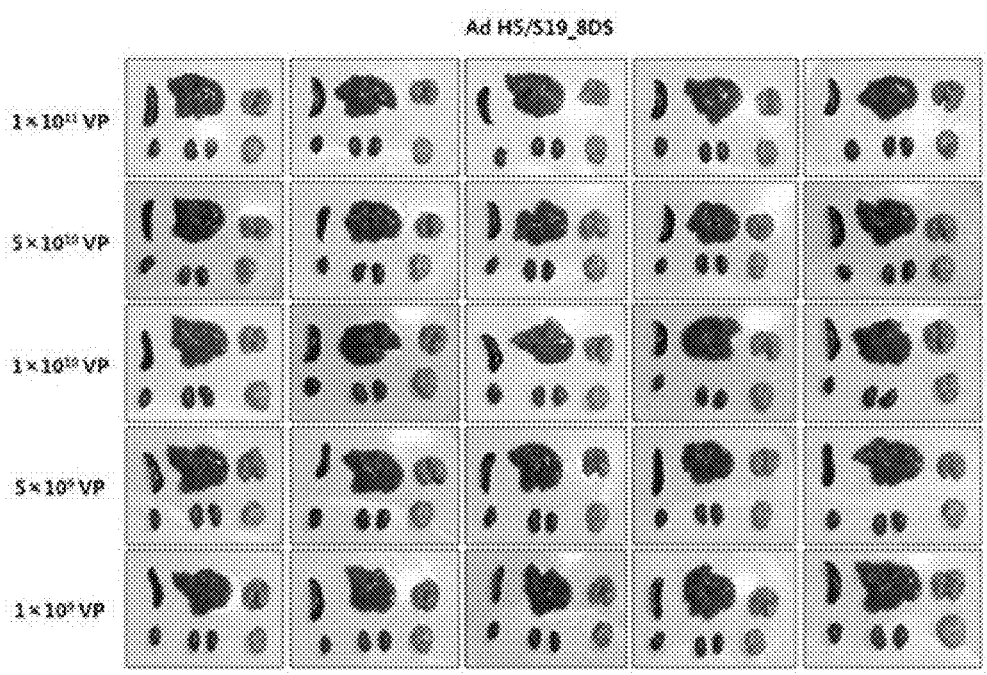
Figure 9:
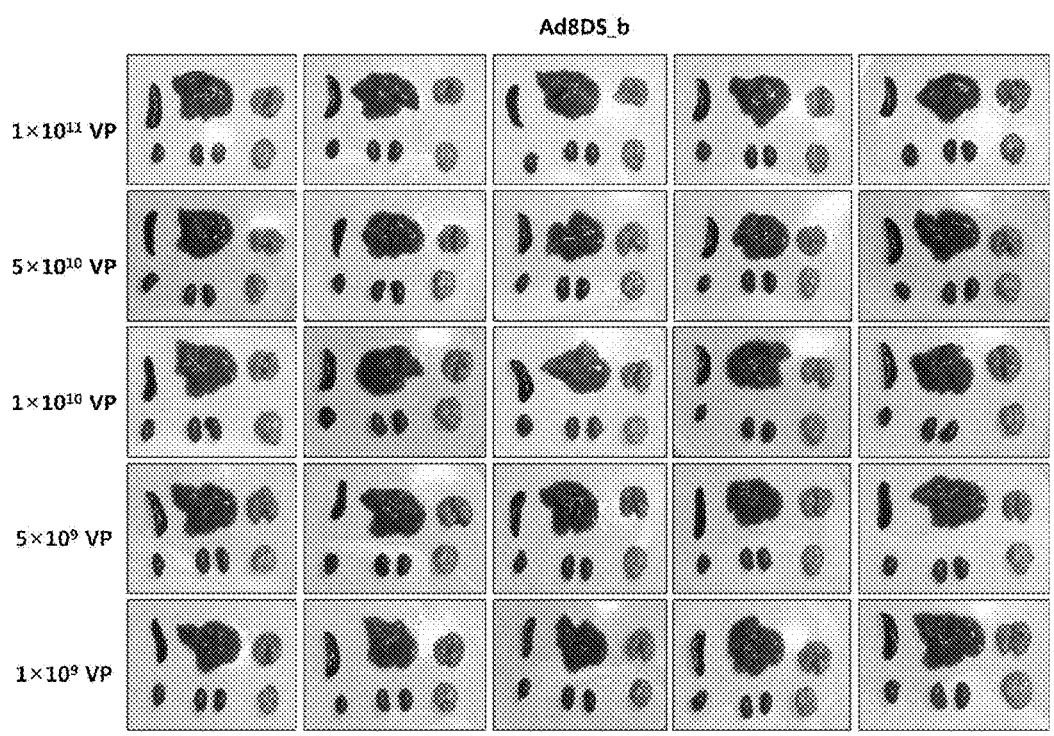

The hexon of SAd19 was studied for toxicity. To this end, the virus was intravenously injected at doses of $1\times10^{11}$ VP, $5\times10^{10}$ VP, $1\times10^{10}$ VP, $5\times10^{9}$ VP, and $1\times10^{9}$ VP, respectively, into five groups of five Balb/c mice which were weighed every other day. At week three and six after the injection, bloods and sera were taken from the mice and analyzed for leukocyte, erythrocyte, platelet and hemoglobin levels, hematocrit, MCV (Mean Corpuscular Volume), MCH (Mean Corpuscular Hemoglobin Concentration), MCHC (Mean Corpuscular Hemoglobin Concentration) and differential leucocyte count. An examination was made of levels of albumin, total protein, SGPT(ALT), SGOT(AST) and ALP for liver function tests, creatinine and BUN for kidney function tests, creatinine kinase for muscle tests, and total cholesterol and glucose for metabolism tests. Of 5 mice in the group which was injected at a dose of $1\times10^{1}$ VP with the human adenovirus serotype 5 virus Ad H5_8DS, four were dead on day 5 while the remaining one was heavily sick. They were found to suffer from hepatocirrhosis by an autopsy, with no abnormality in the other organs. All the other groups were observed to be normal, as examined by autopsy (FIGS. 9(A) and 9(B)).

<6-1> Blood Test

Figure 10B:
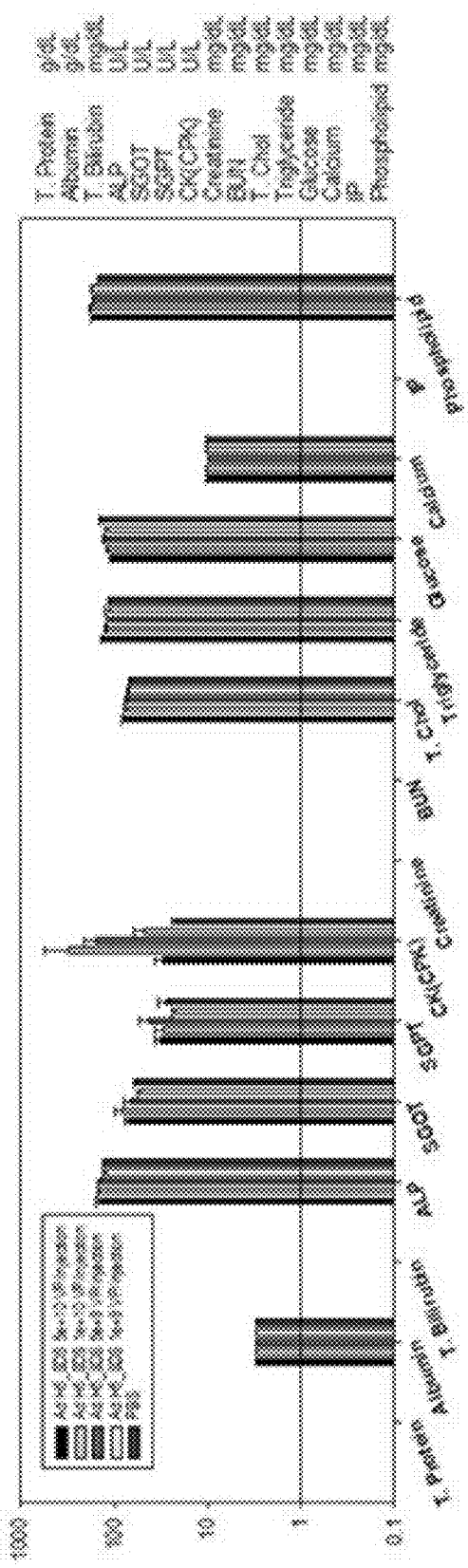
Figure 11B:
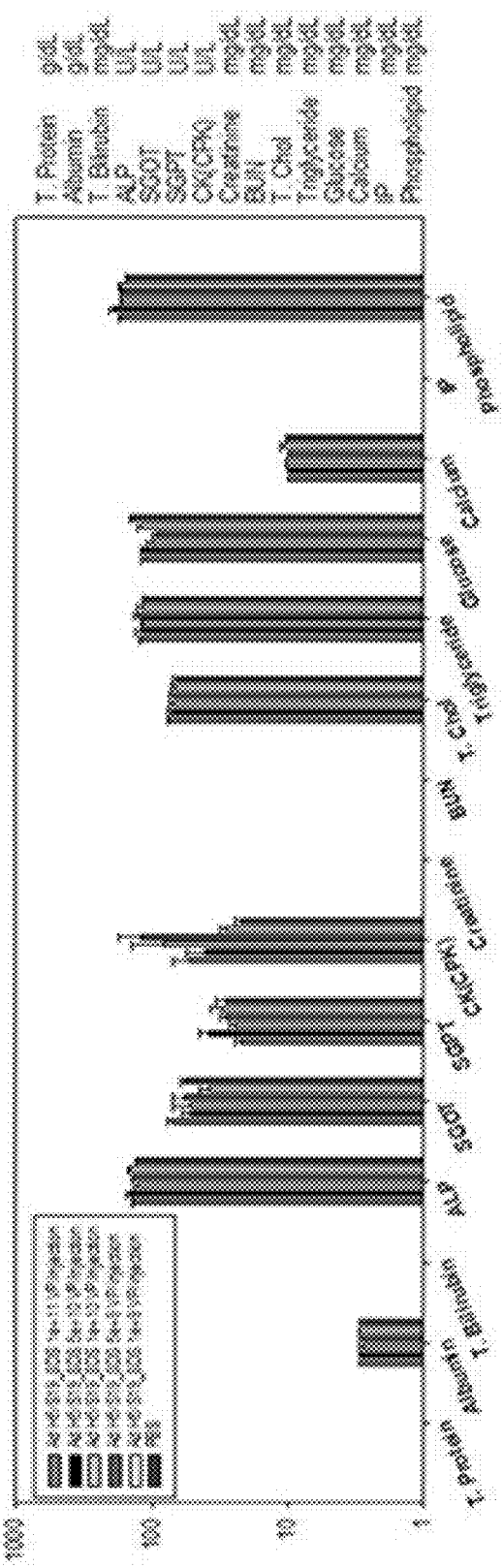
Figure 13:
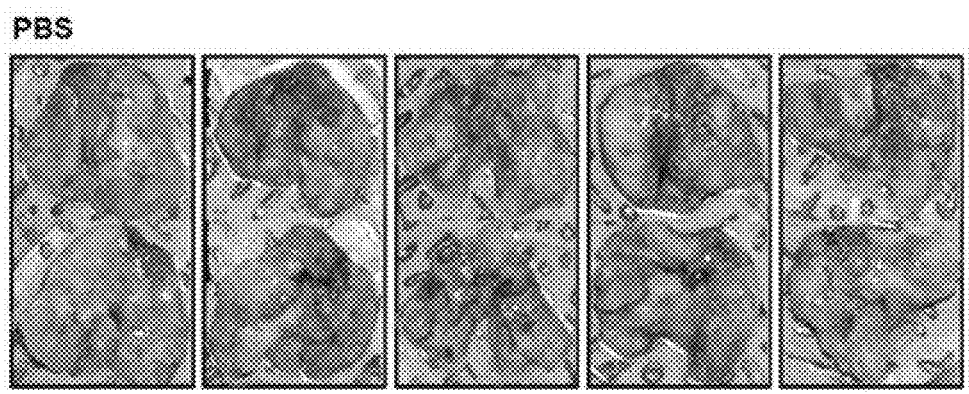
FIGS. 13(A)-13(F): a lung photograph of the animal model for H2172 orthotopic lung cancer autopsied after injection of tumor-specific chimeric adenovirus, Ad H5/S19_8DS depending on the immunization against HAd5.
Figure 13:
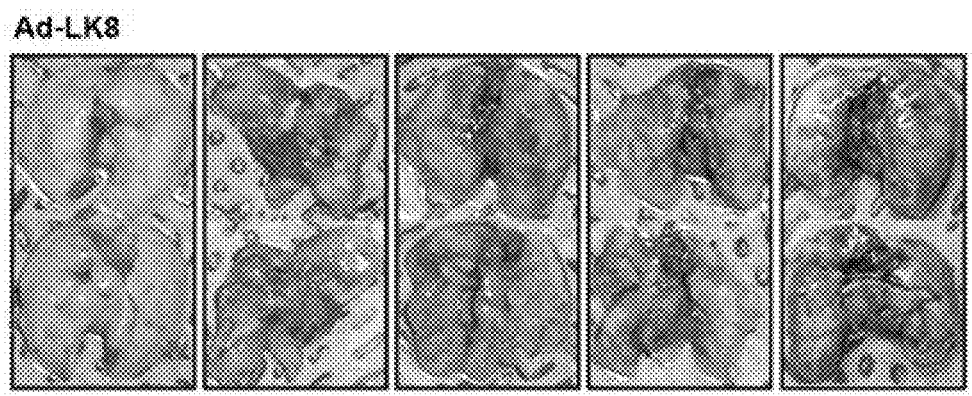
Figure 13:
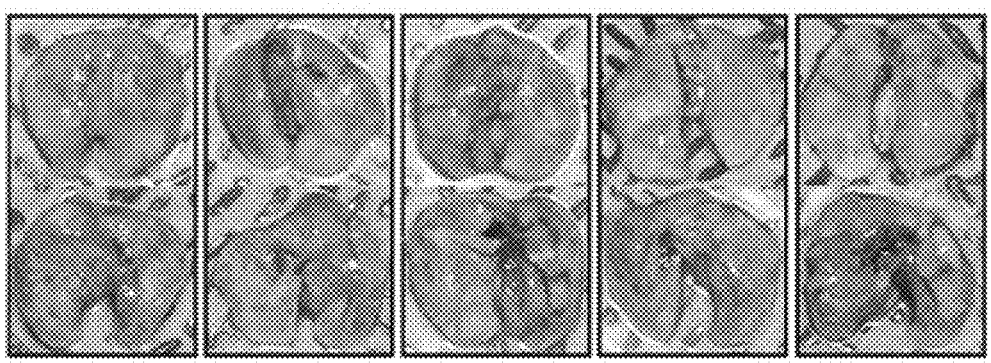
Figure 13:
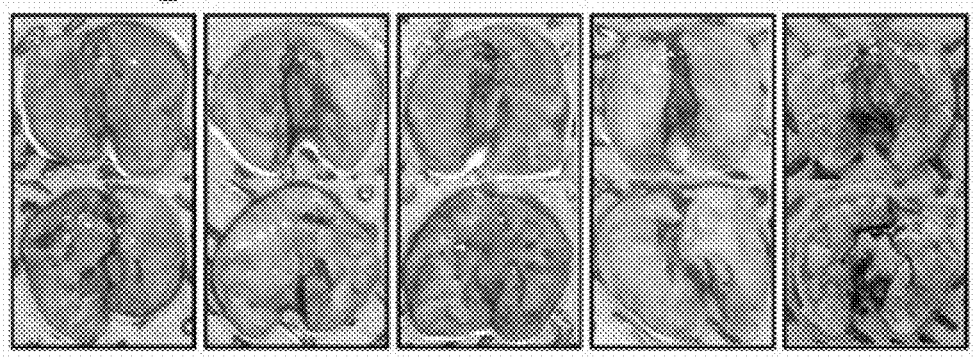
Figure 13:
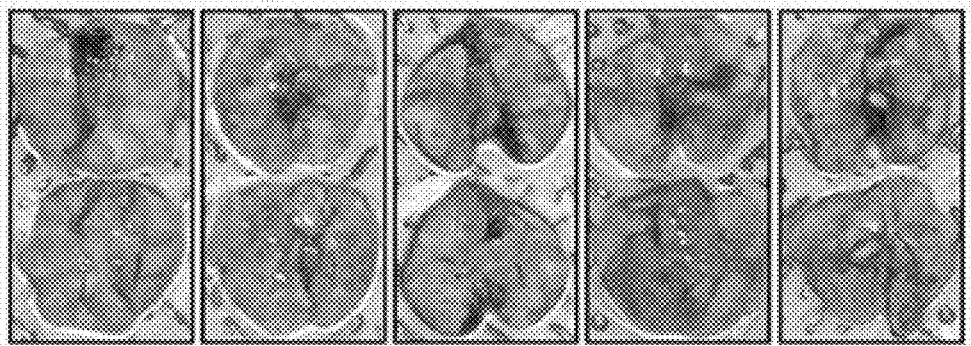
Figure 13:
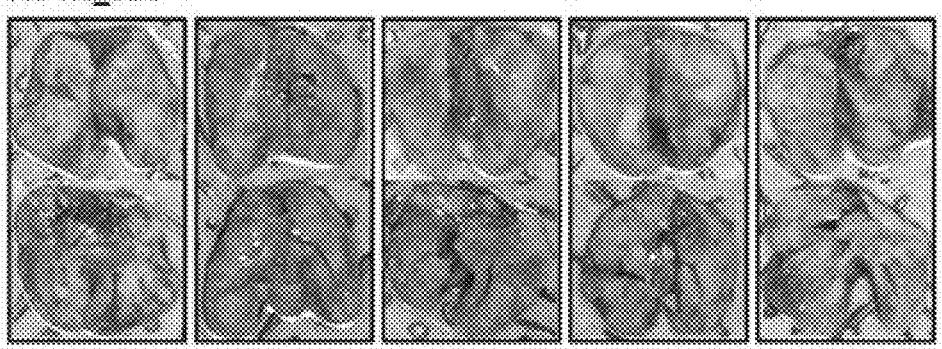
Figure 14:
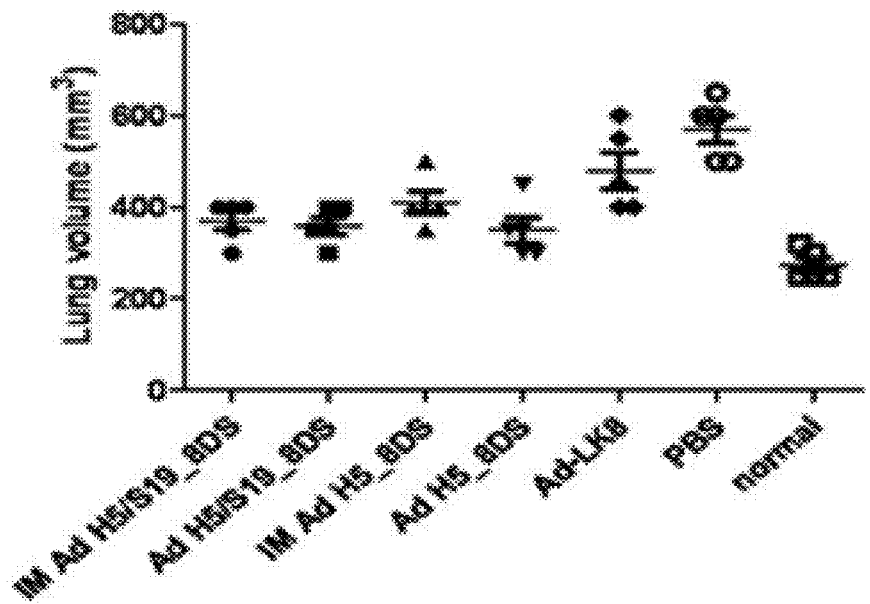
FIGS. 14(A)-14(D): the results of analysing the volume (A), weight (B), the number (C) and the size (D) of the tumors on the lungs of FIGS. 13(A)-13(F).
Figure 14:
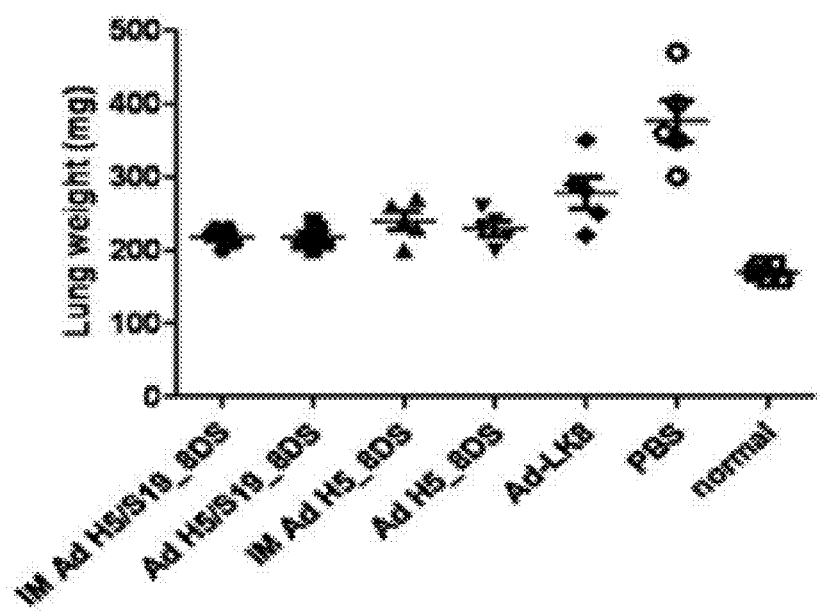
Figure 14:
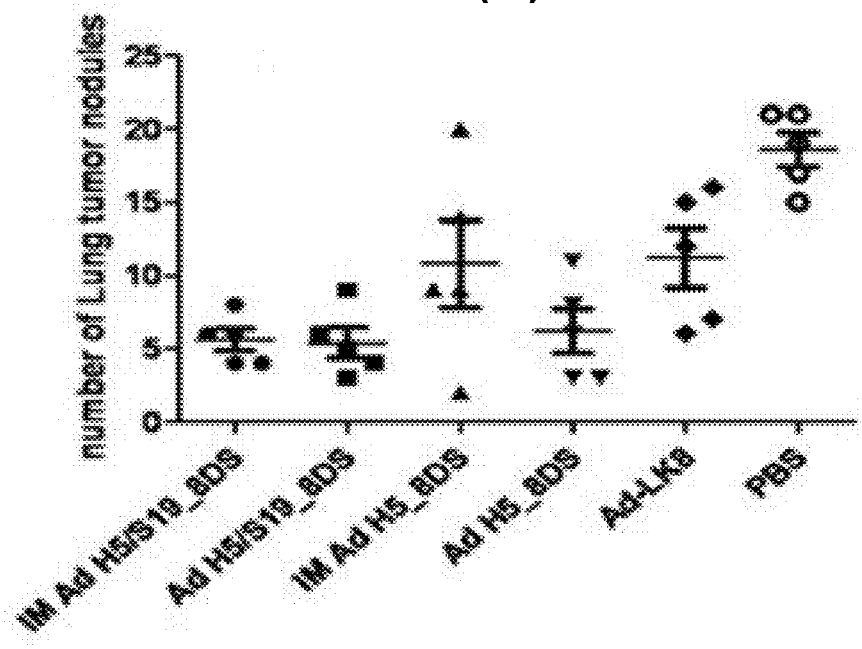
Figure 14:
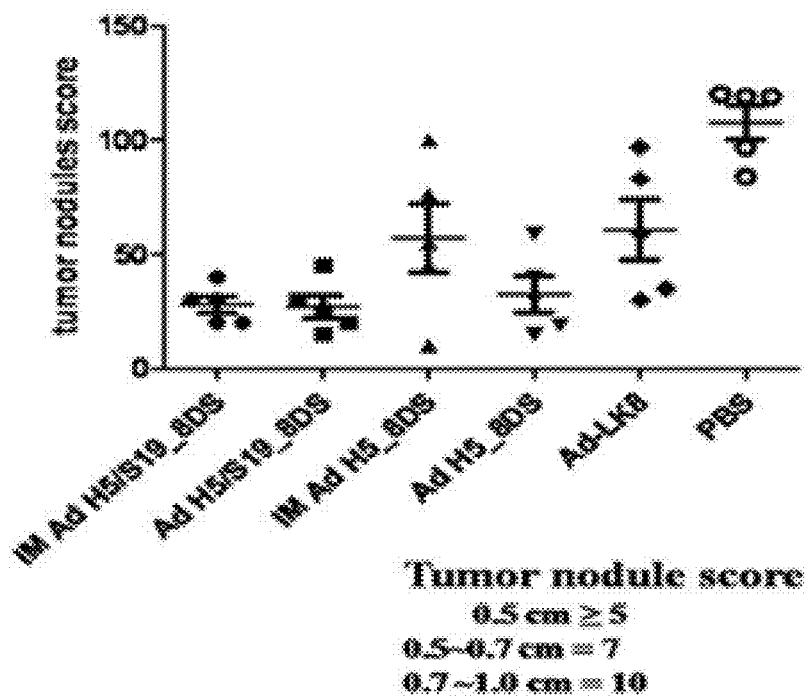

The HAd5, i.e., Ad H5_8DS was intravenously injected at doses of $1\times10^{11}$ VP, $5\times10^{10}$ VP, $1\times10^{10}$ VP, $5\times10^{9}$ VP, and $1\times10^{9}$ VP. On day 5, all of the mice injected with $1\times10^{11}$ VP of the virus were dead. On the other hand, the other groups showed no observations of abnormal toxicity. There were no statistical differences in hematological and blood biochemistry tests between the test groups and the negative control group injected with PBS (FIGS. 10(A) and 10(B)). Abnormal toxicity observations were found in none of the groups to which the chimeric adenovirus having the hexon of SAd19, Ad H5/S19_8DS, was injected at doses of $1\times10^{11}$ VP, $5\times10^{10}$ VP, $1\times10^{10}$ VP, $5\times10^{9}$ VP and $1\times10^{9}$ VP. Also, no statistical differences in hematological and blood biochemistry tests were found between the test groups and the PBS-injected negative control group (FIGS. 11(A) and 11(B)). Hepatotoxicity detected in the group injected with a maximum dose of HAd5 was not observed in the corresponding group injected with the chimeric adenovirus having the hexon of SAd19.

<6-2> Biopsy

The brain, the heart, the liver, the lung, the kidney, the spleen, the uterus and the ovary were excised from the injected mice, fixed with 3.7% neutral formalin, embedded in paraffin, sliced, and stained with H&E. No abnormalities of organs were found in all of the test groups except the group injected with $1\times10^{11}$ VP of human adenovirus serotype. Liver biopsy results showed massive hepatic necrosis in the $1\times10^{11}$ VP-injected group, which was thought to induce acute hepatic failure of which the mice died. This was a general observation of adenoviral hepatotoxicity. As for the chimeric adenovirus having the hexon of SAd19, it did not hepatotoxicity even when injected at a dose of $1\times10^{11}$ VP, indicating that the hexon of SAd19 may be a promising solution to the hepatotoxicity problem caused when HAd5 is used.

EXAMPLE 7

Anti-Tumor Activity of Chimeric Adenovirus Having the Hexon of SAd19 in Animal Tumor Model <7-1> Tumor-Selective, Anti-Tumor Activity of Chimeric Adenovirus on Human Lung Cancer Xenograft Animal Model The non-small cell lung cancer (NSCLC) cell line NCI-H460 was subcutaneously injected at a dose of $5\times10^{6}$ cells into the right flank of immune-deficient Balb/c nude mice to form tumors 50~100 $mm^3$ in size. The mice were randomly divided into four groups of five mice. Mice of control groups were intravenously administered with either replication defective adenovirus carrying LK8 gene, Ad-LK8, at a dose of $1\times10^{9}$ pfu or PBS, three times at regular intervals of two days. As for test groups, they were intravenously injected with Ad H5/S19_8DS in doses of $1\times10^{9}$ pfu and $2\times10^{8}$ pfu, three times at regular intervals. The tumors were measured for size every two or three days to plot tumor growth curves. On Day 24 after the first injection of virus, the group injected at a dose of 1×10$^9$ pfu with Ad H5/S19_8DS exhibited a 74% higher tumor growth inhibition than the PBS-administered group and a 64% higher rate than the Ad-LK8-administered group. On the other hand, the group injected at a dose of 2×10$^8$ pfu with Ad H5/S19_8DS showed a 61% higher tumor growth inhibition rate than the PBS-administered group, and a 48% higher rate than the Ad-LK8-administered group. A 2-way RM ANOVA test revealed statistical significances of both the groups injected with Ad H5/S19_8DS over the PBS-administered group from 17 days after the injection (Day 17 after the injection, P<0.05; Days 21 and 24 after the injection, P<0.01) (FIG. 12).

<7-2> Tumor-Selective, Anti-Tumor Activity of Chimeric Adenovirus on Human Lung Cancer Orthotopic Animal Model Immunized with HAd5

Balb/c nude mice were immunized with HAd5 by two rounds of intramuscular injection at a dose of 1×10$^{10}$ VP for each round at regular intervals of two weeks into the hind leg thereof. Blood taken from the mice was found to contain anti-HAd5 antibody. The NSCLC cell line NCI-H2172 was inoculated at a dose of 1×10$^6$ cells into the tail vein. The naïve and immunized mice were received triple intravenous injections of either Ad-LK8, Ad H5/S19_8DS or Ad H5_8DS on day 7, 9 and 11 after tumor inculcation at an injection dose of 1×10$^9$ pfu. At Week 6, the lung was excised from the mice (FIGS. 13(A)-13(F)). The tumors generated in the lung were counted and divided into groups by size: x≤0.5 cm, 0.5 cm<x≤0.7 cm, and 0.7 cm<x≤1 cm, which were respectively given 5, 7 and 10 points. The tumor generated in the lung was found to count, on average, 18.6 in the PBS-administered, negative control group, and 11.2 in the Ad-LK8-administered group. As for the groups administered with Ad H5/S19_8DS, they were found to have 5.6 and 5.4 tumors, on average, in the lung when immunized or not immunized with the HAd5, respectively. On the other hand, mice in the groups administered with Ad H5_8DS were found to have 10.8 and 6.2 tumors, on average, in the lungs of immunized or naïve mice. Therefore, Ad H5/S19_8DS showed almost the same titers irrespective of immunization, but Ad H5_8DS showed efficacy decreased significantly by anti-HAd5 antibody. Mean lung volumes were measured to be 274 mm$^3$ in normal mice, 570 mm$^3$ in the PBS-administered group, and 480 mm$^3$ in the Ad-LK8-administered group. However, the mouse groups injected with Ad H5/S19_8DS were found to have 370 mm$^3$ lungs and 360 mm$^3$ lungs, respectively, when immunized or non-immunized. There was no significant difference in lung volume between them. In the groups administered with Ad H5_8DS, mean lung volumes were 410 mm$^3$ and 350 mm$^3$, respectively, when immunized or non-immunized. Mean weights of the lungs were measured to be 170 mg in the normal mice, 376 mg in the PBS-administered group and 278 mg in the Ad-LK8-administered group. When injected with Ad H5/S19_8DS, mean lung weight of both the immunized or non-immunized mouse groups was measured to be 218 mg, while mean lung weights of Ad H5_8DS-administered groups were 240 mg for immunized and 230 mg for non-immunized. Turning to the scores gained according to tumor sizes, they were measured to be, on average, 107.8 in the PBS-administered group and 60.8 in the Ad-LK8-administered group. When injected with Ad H5/S19_8DS, the immunized group and the non-immunized group gained 28 and 27 points, respectively. On the other hand, the immunized group and non-immunized group gained 57.2 and 32.6, respectively, when injected with Ad H5_8DS (FIGS. 14(A)-14(D)). Taken together, these data indicate that Ad H5/S19_8DS, irrespective of immunization with HAd5, can exert anti-tumor activity even when intravenously injected.

While the invention has been described with respect to the above specific embodiments, it should be recognized that various modifications and changes may be made to the invention by those skilled in the art which also fall within the scope of the invention as defined by the appended claims.

What is claimed is:

1. A chimeric adenovirus comprising a nucleic acid sequence of a first serotype adenovirus and a nucleic acid sequence of a second serotype adenovirus, said first serotype being different from said second serotype, wherein the nucleic acid sequence of the first serotype adenovirus lacks the hexon encoding sequence and comprises the nucleic acid sequence of the second serotype adenovirus which encodes the amino acid sequence of SEQ ID NO: 16.

2. The chimeric adenovirus of claim 1, wherein the first serotype adenovirus is a human adenovirus.

3. The chimeric adenovirus of claim 2, wherein the human adenovirus is selected from the group consisting of human adenovirus serotypes 2, 3, 5, 11, 24, 26, 30, 34, 35, 36, 41, 48, 49, and 50.

4. The chimeric adenovirus of claim 1, wherein the chimeric adenovirus further comprises a therapeutic transgene.

5. The chimeric adenovirus of claim 1, wherein the therapeutic transgene is selected from the group consisting of a tumor suppressor gene, an antigenic gene, a cytotoxic gene, a cytostatic gene, a suicide gene, an anti-angiogenic gene, and an immune-modulatory gene.

6. The chimeric adenovirus of claim 5, wherein the tumor suppressor gene is selected from the group consisting of a p53 gene, a APC gene, a DPC-4/Smad-4 gene, a BRCA-1 gene, a BRCA-2 gene, a WT-1 gene, a retinoblastoma gene, an MMAC-1 gene, an adenomatous polyposis coil protein, a deleted in colorectal cancer gene, an MMSC-2 gene, an NF-1 gene, an NF-2 gene, an MTS 1 gene, a CDK4 gene, and a VHL gene;

the antigenic gene is a carcinoembryonic antigen gene, CD3 gene, CD 133 gene, CD44 gene, or p53 gene;

the cytotoxic gene is selected from the group consisting of genes encoding a Pseudomonas exotoxin gene, a ricin toxin gene, and a diphtheria toxin gene;

the cytostatic gene is selected from the group consisting of a p21 gene, a retinoblastoma gene, an E2F-Rb fusion protein gene, a gene encoding cyclin-dependent kinase inhibitor, and growth arrest specific homeobox gene;

the suicide gene is selected from the group consisting of genes encoding a herpes simplex virus thymidine kinase, a varicella thymidine kinase, a cytosine deaminase, a purine nucleoside phosphorylase, a beta-lactanase, a carboxypeptidase G2, a cytochrome P450-2B1, a nitroreductase, a beta-glucuronidase and a TNF related apoptosis-inducing ligand;

the anti-angiogenic gene is selected from the group consisting of genes encoding a vascular endothelial growth factor (VEGF), a soluble VEGF receptor, an angiostatin, an endostatin, and an apolipoprotein(a) kringle domain; and the immune-modulatory gene is selected from the group consisting of genes encoding CD16, CTLA-4, IL24 and GM-CSF.

7. The chimeric adenovirus of claim 1, wherein the nucleic acid of the second serotype adenovirus is SEQ ID NO: 3.

8. The chimeric adenovirus of claim 1, wherein the nucleic acid of the second serotype adenovirus is SEQ ID NO: 19.

9. A composition comprising the chimeric adenovirus of claim 1.

10. An isolated host cell comprising the chimeric adenovirus of claim 1.

11. The isolated host cell of claim 10, wherein the isolated host cell is a human cell.

* * * * *